United States Patent [19]
Eggers et al.

[11] Patent Number: 5,419,767
[45] Date of Patent: May 30, 1995

[54] METHODS AND APPARATUS FOR ADVANCING CATHETERS THROUGH SEVERELY OCCLUDED BODY LUMENS

[75] Inventors: Philip E. Eggers, Dublin, Ohio; Hira V. Thapliyal, Mountain View, Calif.

[73] Assignee: Thapliyal and Eggers Partners, Mountain View, Calif.

[21] Appl. No.: 111,367

[22] Filed: Aug. 24, 1993

Related U.S. Application Data

[63] Continuation-in-part of Ser. No. 958,977, Oct. 9, 1992, which is a continuation-in-part of Ser. No. 817,575, Jan. 7, 1992, abandoned.

[51] Int. Cl.$^6$ ............................................. A61M 37/00
[52] U.S. Cl. ................................... 604/114; 604/95
[58] Field of Search ............. 606/41, 31, 28, 194; 604/95, 20, 96–103, 113, 114, 264, 280–281; 128/341–344, 657, 772

[56] References Cited

U.S. PATENT DOCUMENTS

| | | | |
|---|---|---|---|
| 2,050,904 | 8/1936 | Trice | 606/27 |
| 3,460,539 | 8/1968 | Anhalt, Sr. | 128/303 |
| 3,769,984 | 11/1973 | Muench | 128/404 |
| 4,011,872 | 3/1977 | Komiya | 128/303 |
| 4,532,924 | 8/1985 | Auth et al. | 128/303 |
| 4,643,186 | 2/1987 | Rosen et al. | 128/303 |
| 4,646,737 | 3/1987 | Hussein et al. | 128/303 |
| 4,654,024 | 3/1987 | Crittenden et al. | 604/49 |
| 4,660,571 | 4/1987 | Hess et al. | 128/784 |
| 4,672,962 | 6/1987 | Hershenson | 128/303 |
| 4,682,596 | 7/1987 | Bales et al. | 128/303 |
| 4,699,157 | 10/1987 | Shonk | 128/786 |
| 4,709,698 | 12/1987 | Johnston et al. | 604/114 |
| 4,753,223 | 6/1988 | Brener | 604/95 |
| 4,765,331 | 8/1988 | Petruzzi et al. | 128/303 |
| 4,785,823 | 11/1988 | Eggers et al. | 128/692 |
| 4,796,622 | 1/1989 | Lu et al. | 128/303 |
| 4,955,377 | 9/1990 | Lennox et al. | 606/27 |
| 4,955,377 | 9/1990 | Lennox et al. | 128/401 |
| 4,976,711 | 12/1990 | Parins et al. | 606/48 |
| 5,078,684 | 1/1992 | Yasuda | 604/95 |
| 5,114,402 | 5/1992 | McCoy | 604/95 |
| 5,163,938 | 11/1992 | Kambara et al. | 606/47 |
| 5,242,441 | 9/1993 | Avitall | 606/41 |

FOREIGN PATENT DOCUMENTS

WO90/07303  7/1990  WIPO .

*Primary Examiner*—John D. Yasko
*Assistant Examiner*—Manuel Mendez
*Attorney, Agent, or Firm*—Townsend and Townsend Khourie and Crew

[57] ABSTRACT

A catheter system is provided that includes an electrode array near the distal end of the catheter. High frequency current is supplied between the electrodes of the array and a common electrode to cause heating of material lying between the electrodes. The catheter may include means for steering it through the lumen. In a preferred embodiment, the steering means includes a plurality of steering wires in contact with the catheter body. The steering wires may be formed of a shape-memory alloy. Wires of such an alloy may be made to contract when heated above a preselected transition temperature. The wires may be heated by the selective conduction of electrical current through them. Conduction of current through the steering wires is controlled based on the current flowing through the electrodes of the array. An inflatable balloon may be included proximal to the electrode array for dilating the vessel after the occlusion has been penetrated by the electrode array. The balloon may be shielded and protected behind a portion of the catheter having a diameter greater than the diameter of the uninflated balloon disposed about the catheter body. The catheter will include means for protecting the walls of the vessel from exposure to electrical current from the electrodes. This will commonly include switching means or other means for current control. The vessel wall may also be protected by setting the electrodes back some distance from the outer edge of the distal tip.

35 Claims, 19 Drawing Sheets

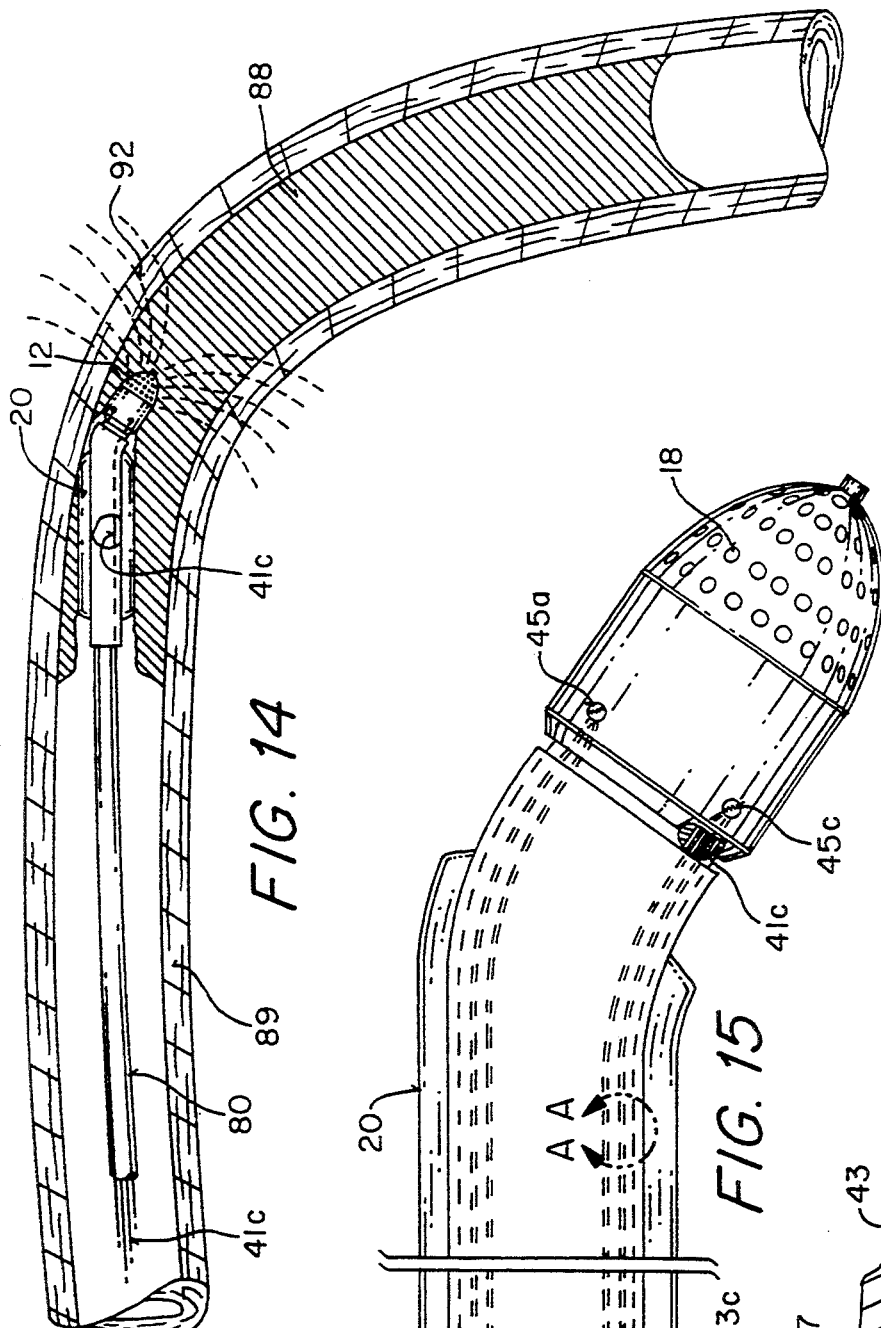

METHODS AND APPARATUS FOR ADVANCING CATHETERS THROUGH SEVERELY OCCLUDED BODY LUMENS

The subject matter of the present application is a continuation-in-part of application Ser. No. 07/958,977, filed on Oct. 9, 1992, which was a continuation-in-part of application Ser. No. 07/817,575, filed on Jan. 7, 1992, now abandoned, the full disclosures of which are incorporated herein by reference.

BACKGROUND OF THE INVENTION

1. Field of the Invention

The present invention relates generally to the construction and use of catheters for interventional and diagnostic procedures. In particular, the present invention relates to methods and apparatus for advancing catheters through restrictions and occlusions within body lumens and cavities.

Atherosclerosis is a form of arteriosclerosis characterized by irregularly distributed deposits on the walls of a patient's arteries. Such deposits frequently fibrose and calcify over time, seriously compromising the patient's health.

A number of catheter-based approaches have been developed for diagnosing and treating atherosclerosis and other forms of arteriosclerosis. The most common interventional technique for treating atherosclerosis is balloon angioplasty, in which a balloon-tipped catheter is introduced into the vascular system and the balloon expanded within a region of stenosis. Other interventional techniques include atherectomy, where, for example, a catheter having a cup-shaped rotating cutter is introduced into the vascular system and used to sever and capture at least a portion of the stenotic material. Other interventional techniques include laser ablation, mechanical abrasion, chemical dissolution, and the like. Catheter-based diagnostic techniques include ultrasonic imaging, in which an ultrasonic transducer disposed at the distal end of a vascular catheter is introduced to the region of stenosis.

With most of these techniques, it is necessary to advance the distal end of the catheter at least partly through the stenosed region before the interventional or diagnostic procedure can be commenced. While such initial advancement is often not a problem, it can be very problematic when the occlusion is severe and little or no lumen remains to receive the catheter. Under such circumstances, it is necessary to at least partly recanalize (create an opening through) the occlusion before the catheter procedure can begin.

A number of methods for recanalizing severe occlusions have been proposed, including the use of hot-tipped catheters, laser catheters, and drill-tipped catheters. In general, these approaches rely on very aggressive treatment of the stenotic material to open up a passage. Such aggressive techniques can expose the blood vessel wall to significant injury, for example, vessel perforation. The risk of injury is exacerbated by the unconstrained path that the catheter can follow.

An improved technique for advancing an angioplasty catheter into and optionally through severe occlusions is described in U.S. Pat. No. 4,998,933 (the entire disclosure of which is hereby incorporated herein by reference), which has common inventorship with the present application. A first electrode is disposed at or near the distal tip of the angioplasty catheter and a second electrode is provided on an electrically conductive guidewire. After the guidewire is at least partly advanced into the stenotic material, a high frequency voltage can be applied between the guidewire electrode and the catheter tip electrode in order to generate heat within the stenotic material lying between said electrodes. The stenotic material is softened as it is heated, thereby allowing easier advancement of the angioplasty catheter.

Although a substantial improvement in the art, the catheter described in U.S. Pat. No. 4,998,933 can cause unwanted short circuiting of electrical energy through the blood and blood vessel wall during the application of the high frequency voltage. The catheter employs a single discrete electrode at its distal tip. So long as the tip electrode fully contacts the stenotic material, the induced heat will be substantially limited to the stenotic material. If the electrode is exposed to the blood vessel wall or blood, however, current will flow through the blood vessel tissue or blood, causing the undesired electrical shorting. Moreover, since both the blood vessel wall and the blood have higher electrical conductivities than the stenotic material, they will carry the current in preference to the stenotic material.

Additionally, the prior art catheters provide no means for steering the tip of the catheter away from the wall of the lumen. By way of example, the stenotic material may be deposited asymmetrically within the vessel lumen resulting in an eccentric stenosis. Conventional catheters will proceed along the residual opening in the lumen, thereby risking damage to the exposed healthy vessel wall if balloon dilatation, thermal, or mechanical means are used to increase the lumen diameter. Also, the occluded vessel may not be straight (e.g., in coronary arterial vessels) necessitating a change in the direction of the advancing catheter tip to avoid thermal or mechanical damage to the vessel wall.

For these reasons, it would be desirable to provide improved apparatus and methods for advancing vascular catheters into and past occlusions in blood vessels and other body lumens. In particular, it would be desirable to provide improvements to catheters generally of the type described in U.S. Pat. No. 4,998,933, to enable the catheter to heat the atheromatous material more selectively. It would be further desirable if such catheters were able to discriminate between the atheromatous mass and the blood vessel wall (preferentially heating and ablating the former) so that the catheter would selectively pass through the atheroma as the catheter is advanced through the lumen of the blood vessel. It would be still further desirable if such catheters incorporated means for steering the catheter tip away from the vessel wall (e.g., away from the media and underlying adventitia layer). In order to improve the capability to advance the catheter through partial or total occlusions while minimizing potential damage to the vessel wall, it would be further desirable to provide a catheter with variable stiffness along its length with the greater stiffness in the portions proximal to the balloon and tip and lesser stiffness in the tip region of the catheter to minimize the danger of perforating the vessel wall.

Some of these goals are addressed in co-pending U.S. patent application Ser. No. 07/958,977, filed Oct. 9, 1992 the complete disclosure of which is hereby incorporated herein by reference. The present disclosure provides still further improvement over previous apparatus and methods.

2. Description of the Background Art

U.S. Pat. No. 4,998,933, has been described above. U.S. Pat. No. 2,050,904 describes a hemostatic probe having a tapered cautery tip at its distal end. European Patent Publication 182,689 and U.S. Pat. No. 4,754,752 describe angioplasty balloon catheters having means for internally heating the balloons. A "hot tip" catheter having a metal tip heated by a laser is described in Cumberland et al. (1986) Lancet i: 1457–1459. U.S. Pat. No. 4,654,024, describes a catheter having an electrically heated tip for melting atheroma. U.S. Pat. No. 4,796,622, describes a catheter heaving a tip that is heated by an exothermic reaction. A catheter having a high speed rotating abrasive element at its distal tip is described in U.S. Pat. No. 4,857,046. U.S. Pat. No. 4,709,698 describes the placement of electrode pairs on the surface of a dilatation balloon to heat atheroma as the balloon is expanded. U.S. Pat. No. 4,955,377, describes an RF heating device employing two spaced-apart electrodes disposed within an inflatable angioplasty balloon. U.S. Pat. No. 5,057,105, describes a hot tip catheter.

A means for manually steering a catheter is described in U.S. Pat. No. 4,543,090. That means utilizes a plurality of temperature-activated memory elements in the distal end of the tubular member. The catheter is steered using a manual "joystick" or other similar control means. Yet another means for steering catheters and scopes is described in U.S. Pat. No. 4,934,340 wherein a contractile wire member is shortened by the passage of electrical current through said wire, thereby causing the catheter to deflect.

SUMMARY OF THE INVENTION

The invention provides apparatus and methods for advancing a catheter through a body lumen and into an occluded region of the lumen. Although the invention will commonly be used in regions of stenosis within blood vessels, the invention may find use in other body lumens as well.

According to one aspect of the invention, a catheter system is provided that includes an electrode array near the distal end of the catheter. High frequency current is applied between the electrodes of the array and a common electrode, or between paired electrodes within the array, to cause heating of selected material lying between the electrodes. A catheter according to the present invention may include means for steering it through the lumen. In a preferred embodiment, the steering means includes a plurality of steering wires in contact with the catheter body.

In preferred embodiments, the steering wires are formed of a shape-memory alloy. Wires of such an alloy may be made to contract when heated above a preselected transition temperature. The wires may be heated by the selective conduction of electrical current through them. In particularly preferred embodiments, the conduction of current through the steering wires is controlled based on the current flowing through the individual electrodes of the electrode array. This will provide a steering means that will tend to steer the catheter through the obstruction in the blood vessel or other body lumen and away from the walls of the vessel.

In another aspect of the present invention, a catheter system will include an inflatable balloon or other interventional structure at a location proximal to the electrode array. The balloon will be useful for dilating the vessel after an occlusion has been penetrated by the electrode array. The balloon (or other structure) will be shielded and protected behind a portion of the catheter having a diameter greater than the diameter of the uninflated balloon disposed about the catheter body. The increased diameter portion of the catheter advantageously comprises the distal tip in which the electrode array is housed.

The catheter will include means for protecting the walls of the vessel from exposure to electrical current from the electrodes. This will commonly include switching means or other means for current control. The vessel wall may also be protected by setting the electrodes back some distance from the outer edge of the distal tip so that a minimum distance is maintained between the vessel wall and the electrodes.

BRIEF DESCRIPTION OF THE DRAWINGS

FIGS. 12C, 13 and 14 illustrates the use of the catheter of FIGS. 12, 12A and 12B in the recanalization of an occluded region within a blood vessel according to the method of the present invention;

FIG. 15 is an enlarged view of the catheter of FIGS. 12–14 illustrating the effect of the steering wires on the curvature of the catheter;

FIG. 15A is a detail view of section A—A in FIG. 15; and

DESCRIPTION OF SPECIFIC EMBODIMENTS

Figure 1:
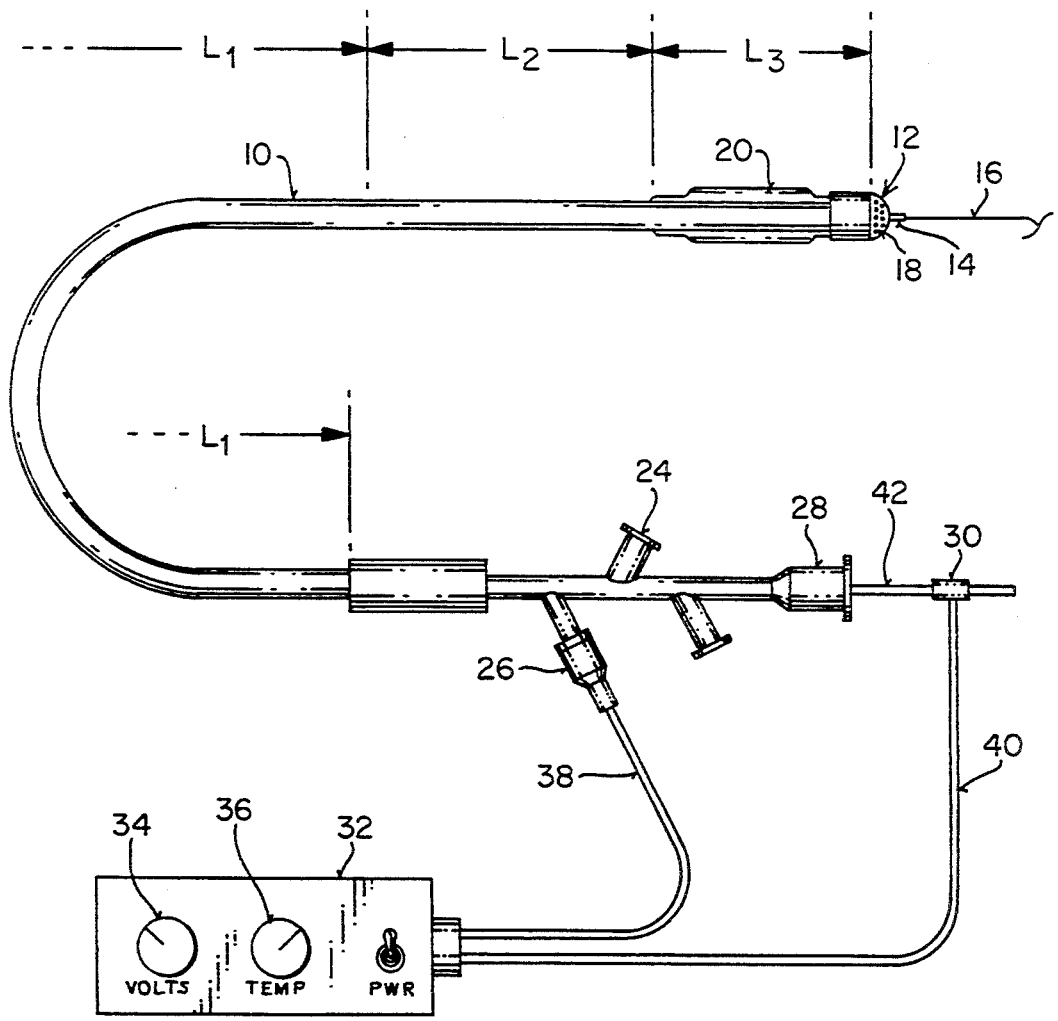
FIG. 1 depicts a catheter system constructed in accordance with the principles of the present invention, wherein the catheter includes a dilation balloon and longitudinal region of varying stiffness.

This invention provides methods and apparatus for selectivity heating a target location within a patient's body, such as solid tissue, a body lumen, or the like, particularly including atheromatous material which partially or fully occludes a blood vessel or other body lumen. In addition to blood vessels, body lumens that may be treated by the method and apparatus of the present invention include the urinary tract (which for example may be occluded by an enlarged prostrate in males), the fallopian tubes (which may be occluded and cause infertility), and the like. Exemplary solid tissues include abdominal tissues, neurological tissues, benign and malignant solid tumors, and the like. Thus, the methods and apparatus may be used in a wide variety of procedures, including intravascular, urological, laparoscopic, arthroscopic, orthopedic, gynecologic, electrothermal, lithotripsy, spinal disc ablation, and the like. For convenience, the remaining disclosure will be directed specifically at the intravascular treatment of blood vessels but it should be appreciated that the apparatus and methods can be applied to other body lumens and passages as well as solid tissue sites for a variety of purposes.

The stenotic material in blood vessels will be, by way of example but not limited to, atheroma or atheromatous plaque. It may be relatively soft (fresh) or it may be calcified and hardened. The invention uses an electrode array including a plurality of independently controlled electrodes distributed over the distal portion of a catheter to apply heat selectively to the stenotic material while limiting unwanted heating of the blood and the surrounding vessel wall. Since the atheromatous mass in the occluded blood vessel is preferentially heated and softened relative to the vessel wall, the path of the advancing catheter tip will naturally be confined in the lumen away from the blood vessel wall.

The electrode array will usually include at least two electrode terminals, usually at least 10 electrode terminals, more usually at least 20 electrode terminals, and sometimes as many as 36 electrode terminals, or more. When current is applied through the electrodes (using either a monopolar or bipolar operational mode as described below), the stenotic material is selectively softened, or weakened, permitting advancement of the catheter to recanalize the blood vessel lumen. Accordingly, this invention provides methods and apparatus for effectively penetrating a partially or totally occluded blood vessel by simultaneously applying both (1) heat to the stenotic material surrounding the tip of the catheter and (2) pressure against the heated stenotic material using the catheter itself. Optionally, subsequent recanalization procedures may be performed using either the same or a different catheter.

The invention typically includes a means for guiding the catheter along a pathway approximating the central region of the occluded blood vessel. The guiding means is usually an electrically conducting wire that may serve as a common electrode for the heating means in the monopolar mode of operation. The guiding means is extensible from the tip of the catheter and is located within and concentric to the catheter conveniently being in the form of a movable or fixed guidewire, usually being a movable guidewire. The electrode array may be disposed proximally to the guiding means (which may act as the common electrode in the monopolar mode of operation) and positioned on or near the tip of the catheter.

Each individual electrode in the array is electrically insulated from all other electrodes and is connected to its own power source or connection to limit or interrupt current flow to the electrode when low resistivity material (e.g., blood) causes a lower resistance path between the common electrode and the individual electrode. The tip of the catheter is thus composed of many independent electrode terminals designed to deliver electrical energy in the vicinity of the tip. Selective heating of the stenotic material may be achieved by connecting each individual electrode terminal and a common or indifferent electrode (e.g., on a guidewire) to an independently controlled power source for monopolar operation. Alternatively, pairs of isolated electrodes in the array may be connected for bipolar operation, with the choice of monopolar or bipolar operation depending entirely on the design of the associated power source. The application of high frequency voltage between the common electrode and the electrode array, or the bipolar electrode pairs, results in the conduction of high frequency current from each individual electrode terminal to the common electrode. Current flow from each individual electrode terminal to the common electrode, or between paired electrodes in the array, is controlled to selectively heat the stenotic material while minimizing undesirable heating of the blood or the vessel wall.

The apparatus takes advantage of the differences in electrical resistivity between the stenotic material (atheromatous mass), blood, and the blood vessel wall. By way of example, for any selected level of applied voltage, if the electrical conduction path between the common electrode (e.g., guidewire) and one of the individual electrode terminals within the electrode array (or between individual paired bipolar electrodes within the array) is blood or blood vessel wall (each having a relatively low electrical resistivity), the current control means connected to or between the individual electrode(s) will limit current flow so that heating of intervening blood or blood vessel wall is minimized. In contrast, if the electrical conduction path between the common electrode and one of the individual electrode terminals (or paired terminals) is atheromatous mass (having a relatively higher electrical resistivity), the current control means connected to that electrode will allow current flow sufficient for the heating and subsequent softening or weakening of the intermediate atheromatous mass.

The application of a high frequency voltage between the common electrode and the electrode array, or paired electrodes within the array, for appropriate intervals of time substantially weakens the selectively heated atheromatous mass, allowing the catheter to penetrate and pass through the obstruction, thus recanalizing the blood vessel. Once the partially or fully occluded blood vessel has been opened to allow passage of the catheter, the catheter can be advanced to position a dilatation balloon (or other interventional or diagnostic element) within the occluding material. The dilatation balloon can then be used for angioplasty treatment in a conventional manner.

In addition to an angioplasty balloon, the catheters of the present invention may include a variety of other interventional and/or diagnostic structures disposed proximally to the electrode array at the distal tip. For example, the catheter could include inflatable or non-inflatable drug delivery membranes or matrices on its exterior surface. In this way, the drug delivery membrane could be passed into an atheromatous mass behind the electrode tip and a therapeutic agent, such as a clot-dissolving drug, released directly into the mass.

Direct heating of the stenotic material by conduction of high frequency current softens the material over a distributed region. The volume of this distributed region may be precisely controlled, for example, by the geometrical separation between the common electrode (e.g., the guidewire) and the electrode array. The rate of heating of the stenotic material is controlled by the applied voltage level. The use of high frequency current for heating minimizes induced stimulation of muscle tissue or nerve tissue in the vicinity of the mass being heated. In addition, high frequencies minimize the risk of interfering with the natural pacing of the heart when the catheter of the present invention is used in the coronary arteries.

The power applied between the common electrode and the electrode array, or paired electrodes within the array, will be at high frequency, typically between about 50 kHz and 2 MHz, usually being between about 100 kHz and 1 MHz, and preferably being between about 200 kHz and 400 kHz. The root mean squared (RMS) voltage applied will usually be in the range from about two volts to 100 volts preferably being in the range from about five volts to 90 volts, and more preferably being in the range from about seven volts to 70 volts. Usually, the voltage applied will be adjustable, frequently in response to a temperature controller which maintains a desired temperature at the interface between the electrode array and the stenotic material. The desired temperature at the interface between the electrode array and the stenotic material will usually be in the range from about 38° C. to 100° C., more usually from about 38° C. to 80° C., and preferably from about 40° C. to 70° C.

A particular advantage of the present invention is that the heating means can be configured to a wide range of catheter sizes appropriate to the particular size of the occluded blood vessel or other body lumen or cavity being recanalized, typically in the range of diameters from 0.04 to 0.4 inches. The present invention can also incorporate a guidewire which can function as both a means for controlling and guiding the path of the catheter in the conventional manner, as well as to concentrate the thermal power density dissipated directly into the stenotic material by serving as the common electrode in monopolar operation.

The preferred power source of the present invention can deliver a high frequency voltage selectable to generate power levels ranging from several milliwatts to 100 watts, depending on the size of the stenotic material being heated, the size of the vessel being recanalized, and the rate of advancement of the heating means through the stenotic material. The power source allows the user to select the voltage level according to the specific requirements of a particular angioplasty or other procedure.

The power source will typically be current limited or otherwise controlled so that undesired heating of blood, blood vessel wall, and other low electrical resistance materials does not occur. In some embodiments of the present invention, current limiting resistors are placed in series with each independent electrode, where the resistor is 'sized' to provide an at least equal, and preferably greater, resistance than would normally be provided by the stenotic material. Thus, the electrode sees a substantially constant current source so that power dissipation through a low resistance path, e.g., blood, is substantially diminished.

As an alternative to current limiting resistor, inductors or capacitors may be used to limit current flow to the electrode in response to a change in the load impedance.

As an alternative to current limiting elements, such as resistors, inductors, and capacitors, a controlled power supply may be provided which interrupts the current flow to an individual electrode in the array when the resistance between that electrode and the common electrode falls below a threshold level. The control could be implemented by placing a switch in series with each electrode, where the switch is turned on and off based on the sensed current flow through the electrode, i.e., when the current flow exceeds a preselected limit, the switch would be turned off. The current limit could be selectable by the user or preset at the time of manufacture of the power source. Current flow could be periodically sensed and re-established when the stenotic material resistance is again present. Particular control system designs for implementing this strategy are well within the skill in the art.

Figure 2:
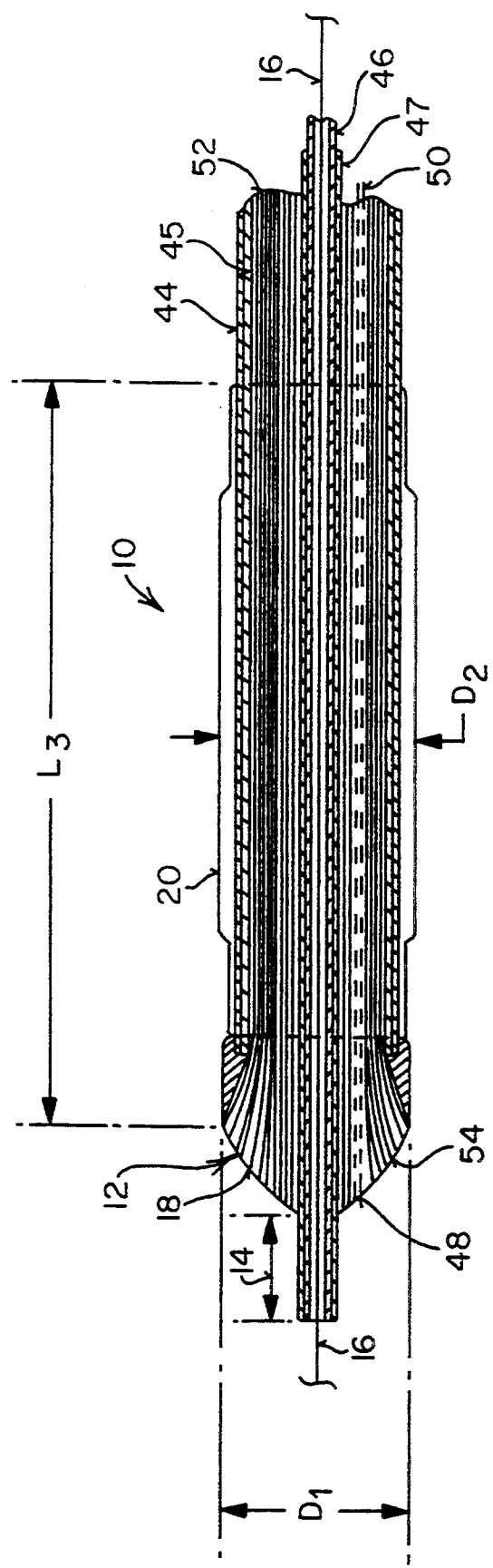
FIG. 2 is a sectional view of the distal end of the catheter of FIG. 1 illustrating an enlarged distal tip.

In an exemplary monopolar embodiment as shown in FIG. 1, a catheter 10 includes a guidewire 16, which functions both as a means for guiding the catheter into the intended position, and as a common electrode. The entire guidewire may be an electrode, or the guidewire may include an electrode. Referring to FIGS. 1 and 2, the catheter 10 also includes an array of electrode terminals 18 disposed on the distal tip 12 of the catheter 10. The electrode terminals 18 are electrically insulated from each other and from the common electrode 16. Proximally from the tip 12, the catheter 10 includes a conventional angioplasty balloon 20 generally concentric with the body of the catheter 10. Said catheter 10 may be constructed having zones of varying flexibility (or conversely, stiffness) along the catheter body length. It is advantageous, for example, to have greater flexibility (i.e., lesser stiffness) at the distal end of catheter 10 (see region $L_3$ in FIGS. 1 and 2) in order to (1) increase the trackability of the catheter along a lumen with changing directions and (2) decrease the possibility of damaging the vessel wall while forcing catheter 10 through the lumen. Catheter regions $L_1$ and $L_2$ of lesser flexibility (i.e., greater stiffness) may likewise be provided proximal to the more flexible region $L_3$ to increase the capability to advance catheter 10 through a partial or total occlusion. In the embodiment illustrated in FIG. 1, catheter 10 has three zones wherein, region $L_1$ is stiffer than region $L_2$ and region $L_2$ is stiffer than region $L_3$.

Still referring to FIGS. 1 and 2, each of terminals 18 is connected to an active control network within a monopolar power controller 32 by means of individually insulated conductors 52. The proximal portion of catheter 10 is also equipped with a fluid port 24 communicating with balloon 20. The guidewire is axially movable in an electrically insulating guidewire lumen tube 46, said lumen tube 46 being contained in, and concentric to, the body of catheter 10. The proximal end 42 of the guidewire is sealed against fluid leaks by a fluid seal 28. The proximal portion of catheter 10 also has a connector 26 for providing electrical connections to the active control network within control means 32.

Power source and controller 32 provide a high frequency voltage to electrode terminals 18 by means of a cable 38 connectable to connector 26. Power source 32 has a selection means 34 to change the applied voltage level as well as an adjustment means 36 for selection of the highest temperature at the tip 12 of catheter 10 during its use, as explained later. Finally, the proximal portion of the guidewire electrode 42 is connected to the power source 32 by a detachable connector 30 and cable 40.

The catheter 10 may also be used, without substantial modification, in bipolar procedures where selected electrode terminals 18 in the array 16 may be connected to opposite polarity connections within a bipolar power control means (not illustrated). The bipolar power control means will be very similar to the monopolar controller 32, except that no separate cable 40 will be provided for the guidewire. Instead, cable 38 will be modified to provide bipolar connection to paired terminals 18 in any desired pattern. Typically, but not necessarily, the paired terminals will be spaced-apart from each other and will not be immediately adjacent to each other.

Figure 3:
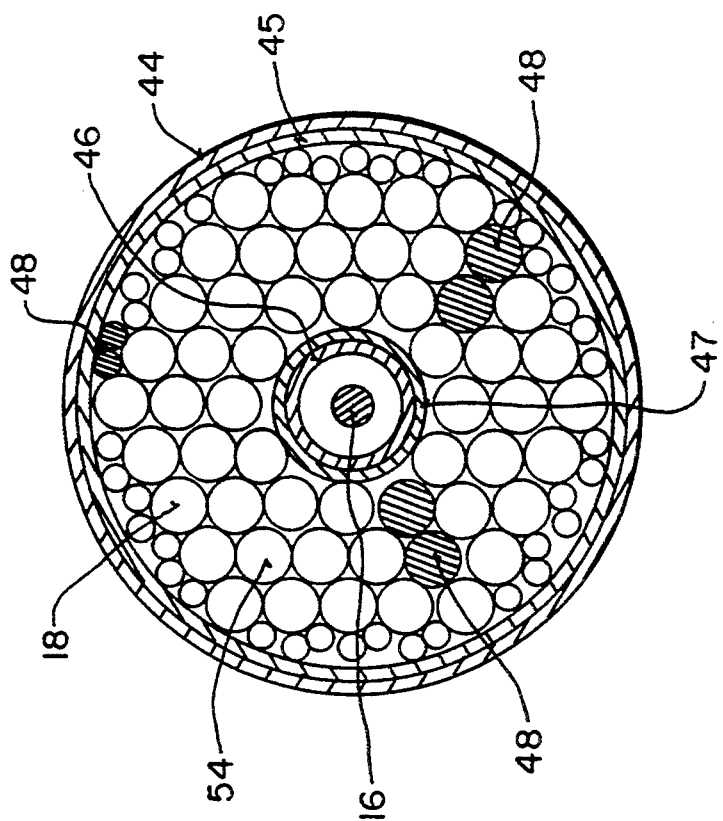
FIG. 3 is an end view of the distal tip of the catheter of FIGS. 1 and 2.

In the embodiment shown in FIGS. 1, 2, and 3, temperature sensors 48 are provided in the distal tip 12 of the catheter 10, typically in the form of thermocouple pairs (e.g., Chromel® and Alumel®). Temperature sensors 48 are connected to power source 32 by thermocouple wires 50 extending the length of catheter 10 and by the cable 38 connected through the connector 26. Temperature sensors 48 at the tip 12 of catheter 10 are connected to a feedback control system in power source 32 to adjust the power output so that the user selectable temperature is not exceeded during use of the catheter in recanalization of an occluded blood vessel. Power output could be controlled by any conventional technique, such as control of voltage, current, duty cycle, or the like. The selectable temperature is selected by the user by adjusting selector 36 provided in the power source 32.

Referring to FIG. 2, the distal tip 12 of the catheter 10 of the preferred embodiment houses the exposed ends of electrode terminals 18 and temperature sensors 48. Electrode terminals 18 and temperature sensors 48 are secured in a matrix of suitable insulating material (e.g., epoxy) 54 formed in a generally tapered or hemispherical shape, preferably being a conical or "nose cone" configuration. Catheter tip 12 preferably has a diameter at least as large as balloon member 20 when the balloon is not inflated. Proximal to the tapered tip 12, the temperature sensor wires 50 and electrode wires 52 are contained in a jacket 44 of cylindrical shape covering the length of catheter 10.

Referring to FIGS. 2 and 3, catheter 10 includes an electrically conducting member 45 disposed around electrode wires 52 and within the interior of jacket 44. Also, an electrically conducting member 47 is disposed around the electrically insulating guidewire lumen tube 46. Electrically conducting members 45 and 47 are maintained at the same electrical potential as the electrode lead wires 52, thereby minimizing electromagnetic interference between the electrode leads 44 and the common electrode guidewire 16. An arrangement of electromagnetic shielding means 45 and 47 extending over the length of catheter 10 allows for accurate measurement of electrical impedance between any electrode terminal 18 and the common electrode (guidewire) 16.

Accurate measurement of the impedance between each electrode terminal 18 and the common electrode 16 provides a means for distinguishing between higher resistivity media (e.g., atherosclerotic media) and lower resistivity tissue (e.g., healthy vessel wall). The measurement of the electrical impedance in the pathway between each electrode 18 and the common electrode 16 can be used to selectively apply power to those electrodes 18 having impedance levels within the range of the target tissue (atheromatous media). As used herein, electrical impedance is defined broadly to include both resistance and reactance (the latter being combined inductance and capacitance).

An end view of the catheter 10 at the tip 12 is illustrated in FIG. 3. Referring to FIGS. 2 and 3, electrode terminals 18 are electrically insulated from each other and from temperature sensors 48, and are secured together in a bundle by the electrically insulating material 54. Proximal to the tip 12, the temperature sensor wires 50 and electrode wires 52 are contained in a suitable jacket 44 of cylindrical shape running the length of catheter 10. The central portion of catheter 10 contains the electrically insulating guidewire lumen tube 46, which provides a lumen for the guidewire 16. The distal end of tube 46 optionally extends beyond the tip 12 to provide a tip offset 14. The intended purpose of tip offset 14 is to provide a minimum separation between the common electrode on guidewire 16 and array of electrodes 18, usually being at least 0.02 inches, more usually being at least 0.15 inches, and sometimes being 0.25 inches or more.

Figure 4:
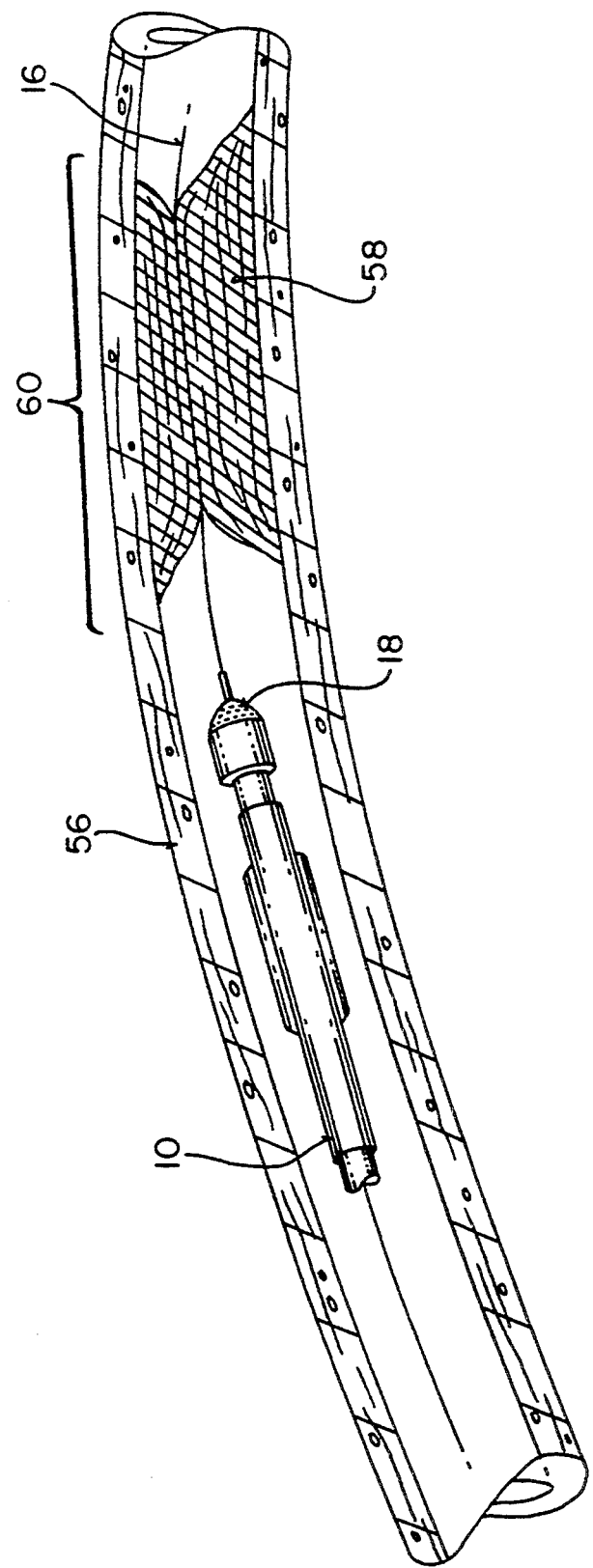
FIGS. 4–8 illustrate the use of the catheter of FIGS. 1-3 in the recanalization of a stenosed region within a blood vessel according to the methods of the present invention.

FIG. 4 illustrates how catheter 10 can be applied to recanalize a blood vessel 56 occluded by atheromatous plaque 58. In this case, guidewire 16 is first advanced to the site of the atheromatous plaque 58. The catheter 10 is then moved over guidewire 16 to contact a leading edge of the plaque. Next, guidewire 16 is advanced through the plaque 58 under fluoroscopic guidance exposing a length 60 of the guidewire that is electrically conducting.

Figure 5:
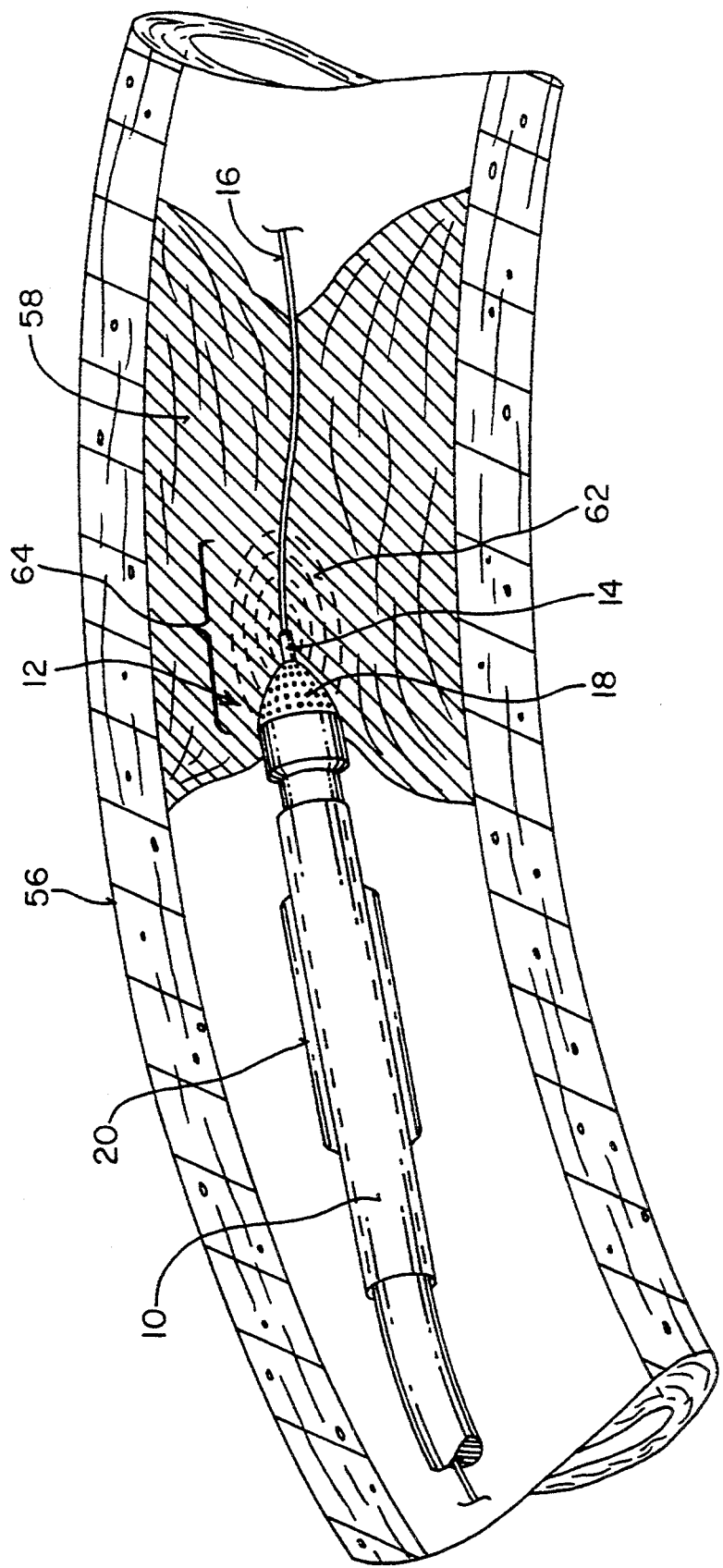

Referring next to FIG. 5, distal tip 12 of catheter 10 housing the array of electrode terminals 18 is urged against the atheromatous plaque 58. A high frequency voltage is applied between the common electrode on guidewire 16 and each of the electrode terminals 18. The resulting electrical current flows between the common electrode 16 and the electrode terminals 18 through the atheromatous plaque 58, as illustrated by current flux lines 62. Due to the electrical resistance of the atheromatous plaque 58 and the capability to selectively energized electrodes 18 in contact with higher resistivity media, the localized current flow heats the plaque 58 in a zone 64. The localized heating is controlled by varying the level and duration of the high frequency voltage.

Tip offset 14 maintains a minimum distance between the electrodes 18 and the common electrode on guidewire 16. The zone of heating 64 within the plaque 58 is defined by current flux lines 62. The atheromatous plaque material softens in the heated zone 64, which facilitates the forward axial advancement of the catheter tip 12 through the heated zone. Movement of the tip 12 displaces the plaque material, thereby recanalizing the previously occluded blood vessel 56. The catheter 10 is advanced through the softened plaque until a channel is created in the occluding mass. The catheter 10 is withdrawn leaving a vessel recanalized allowing an improved flow of blood therethrough.

After catheter 10 has been advanced through the plaque, balloon 20 can be positioned within the atheromatous media and inflated with an appropriate fluid to pressures suitable to effect conventional angioplasty.

Figure 6:
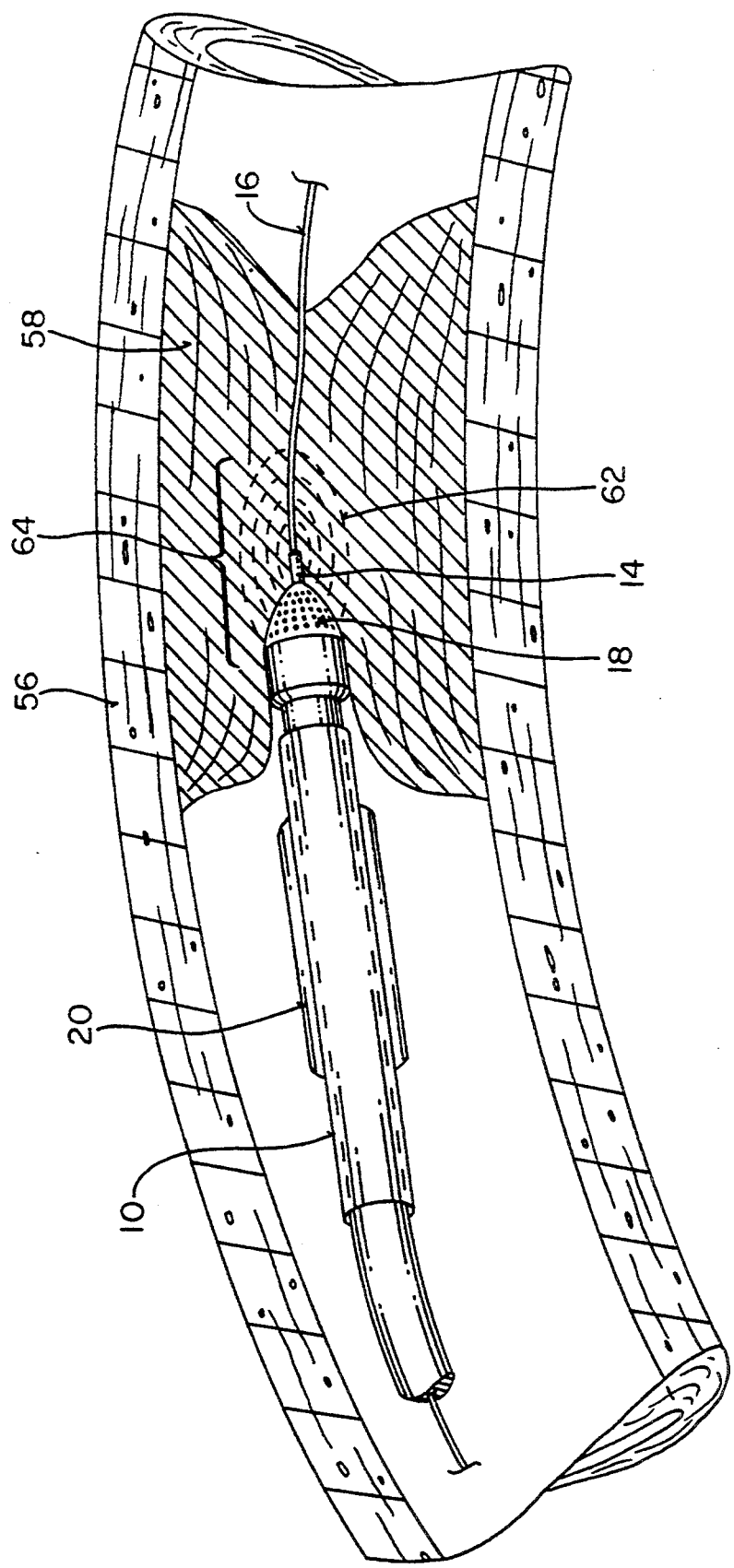

There are situations in which a guidewire cannot be completely advanced across a stenosed region 58, as illustrated in FIG. 6. In such cases, the common electrode (guidewire) 16 is partially penetrated into the atheromatous plaque 58' to the extent possible. The array of electrodes 18 is contacted against the wall of plaque 58', and the tip offset 14 ensures a minimum spacing between the common electrode 16 and the electrode array so that some heating of plaque will occur. The catheter 10 and the common electrode 16 can then be alternately advanced until a channel is created through the entire region of plaque 58'. Those electrodes 18 in contact with higher resistivity material (e.g., atheromatous media) will be selectively energized thereby preferentially heating and softening the plaque 58' while minimizing any heating of lower resistivity material (e.g., vessel wall) that may come in contact with electrodes 18. Once again, conventional balloon angioplasty can be performed once the deflated balloon 20 has been advanced across the plaque 58'.

Figure 7:
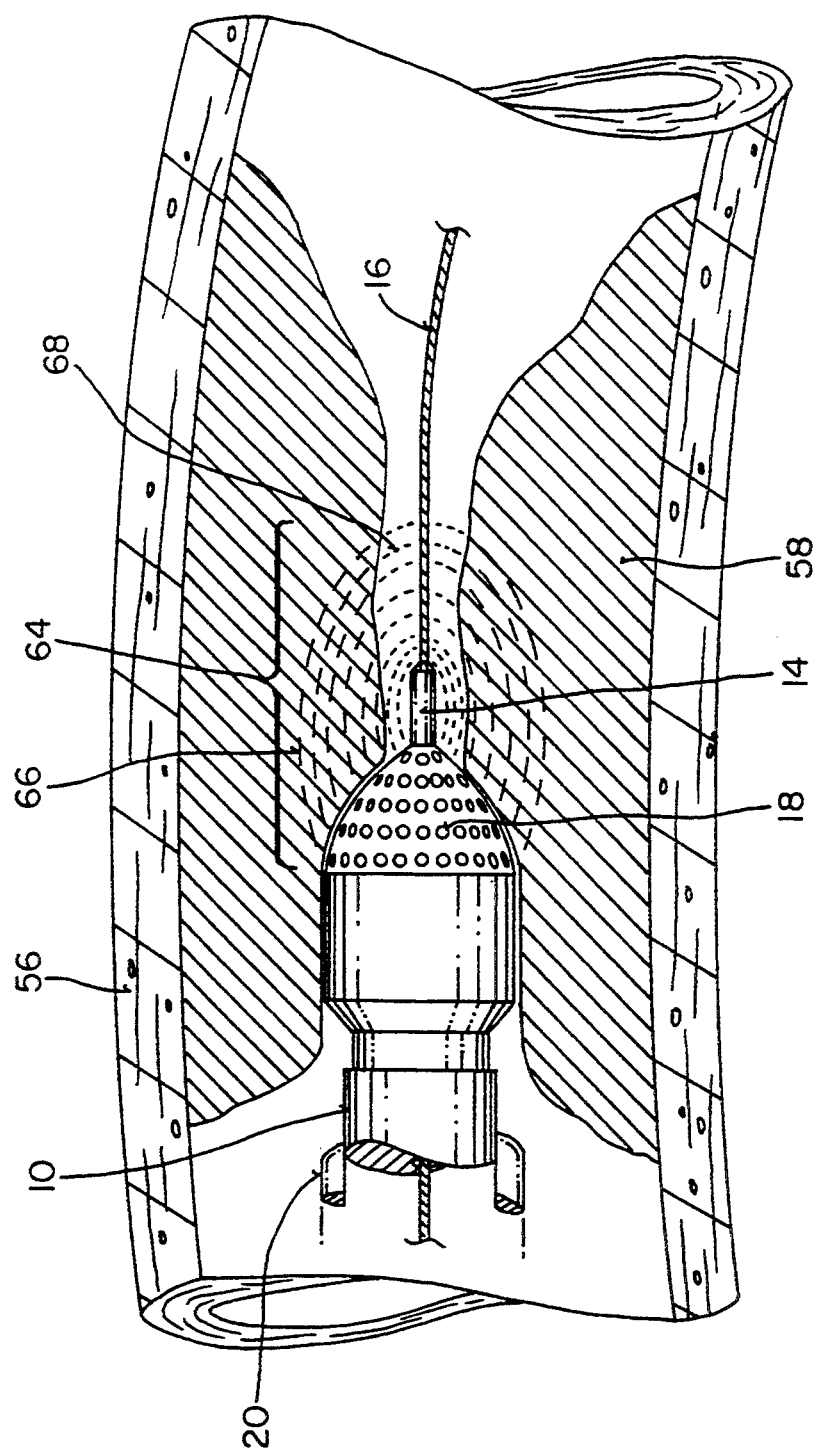
Figure 8:
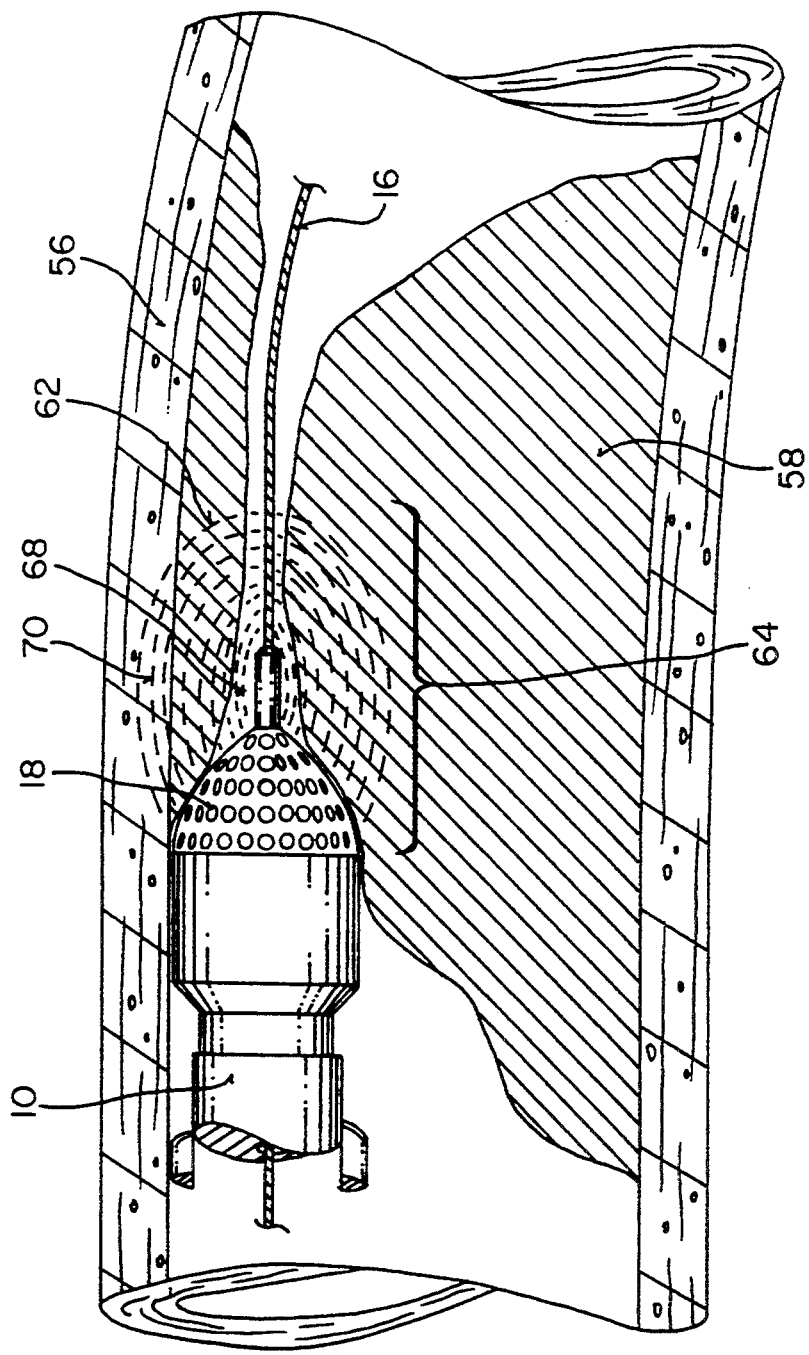

Catheter 10 has the ability to deliver electrical energy selectively to the intended areas, i.e., the atheromatous material, and not to the blood or the blood vessel. Such directed energy transfer results in selective heating of the atheromatous material which allows the catheter to be "self-guiding" as described above. When the tip 12 of catheter 10 is pressed against a region of stenotic material, some of the electrode terminals 18 will be in contact with atheroma, while other electrode terminals may be in contact with blood, and yet others may be in contact with blood vessel wall. These situations are illustrated in FIGS. 7 and 8. Each of the electrode terminals 18 experiences an electrical impedance characteristic of the material disposed between the individual electrode terminal and the common electrode. The catheter takes advantage of the fact that the electrical resistivity of typical atheroma is higher than that of blood or blood vessel wall. Thus, if the current passing through each of the electrode terminals 18 is limited to a substantially constant value, a region of higher electrical resistivity will experience more heating (power = $I^2R$, where I is the current through resistance, R) than a region of lower electrical resistivity. Furthermore, the apparatus may individually monitor the electrical impedance between each electrode 18 in the catheter tip array of electrodes and the guidewire 16 and energize said electrode 18 only if the measured electrical resistance is above a preselected level. Therefore, by either one or a combination of both means described above the atheromatous plaque of the stenotic region will be selectively heated and softened while the blood and blood vessel wall will experience a minimal rise in temperature. Thus, the catheter will selectively advance through the atheroma.

The heating selectivity of the present invention may be accomplished by establishing a preselected level or user selected threshold level of electrical resistance in the pathway of the electrical current 62 between the common electrode (guidewire) 16 and each of the electrode terminals 18 in the electrode array located at the tip 12 of catheter 10. By way of example, the electrical resistivity of blood at body temperature is in the range from 148 to 176 ohm-cm at a frequency up to 120 kHz (Geddes et al., (1967) *Med. Biol. Eng.* 5:271-293). The electrical resistivity of human cardiac and skeletal muscle (which approximates the structure of the blood vessel wall) is in the range of 100 to 456 ohm/cm at frequencies in the range 100 to 1000 kHz (Geddes et al., (1967), supra).

In contrast, atheromatous mass generally consists of fat-like deposits containing cholesterol, lipids, and lipophages. Due to its primarily fat-like composition, the atheromatous mass has a relatively high electrical resistivity as compared with blood. The electrical resistivity of fat-like substances in humans has been reported in the range of 1,000 to 3,000 ohm/cm at frequencies ranging from 100 to 1,000 kHz (Geddes et al., (1967), supra). This invention utilizes the inherent two to tenfold difference in electrical resistivities to selectively energize and heat the atheromatous plaque in a blood vessel.

Figure 9:
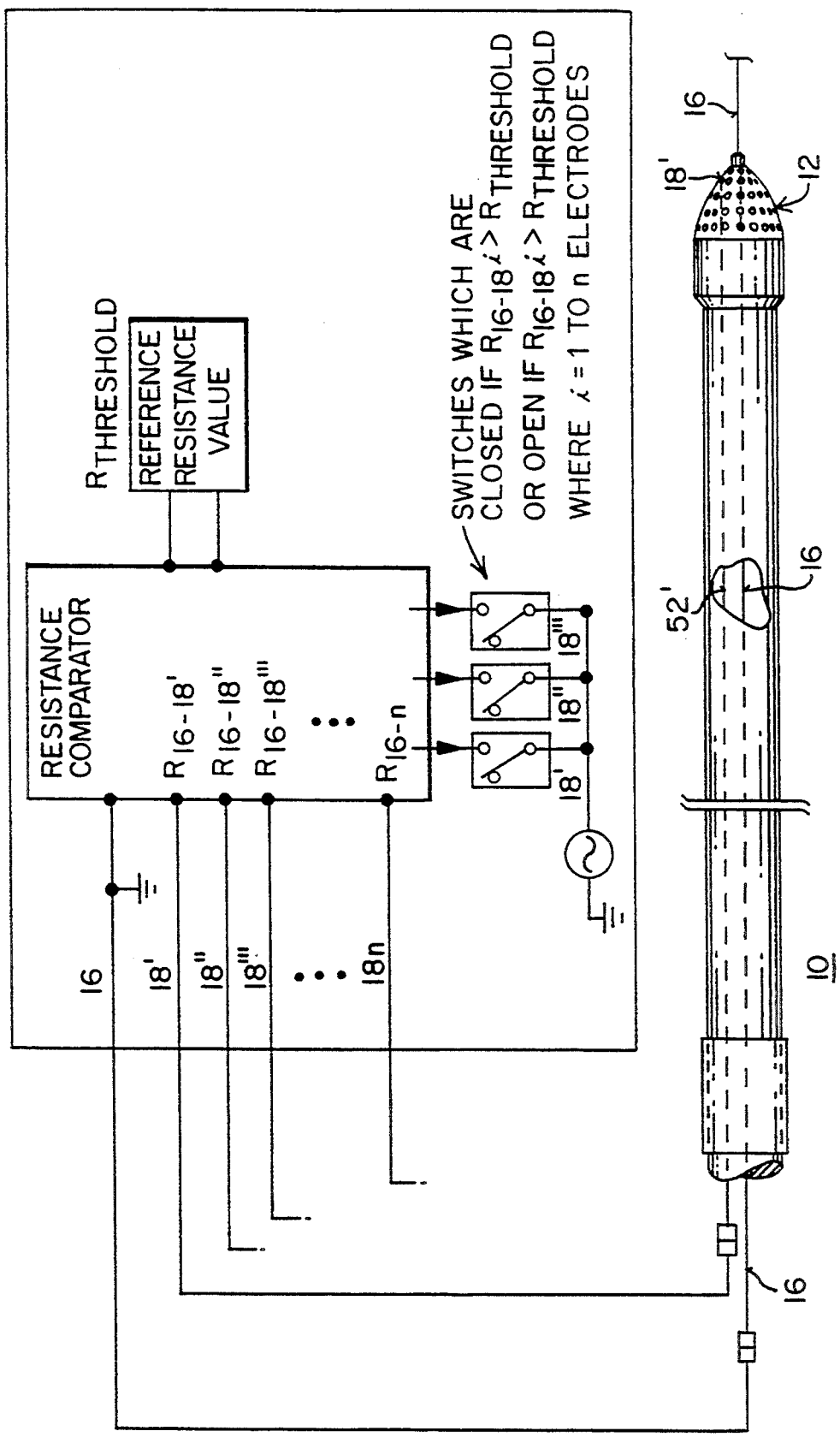
FIG. 9 is a schematic illustration of a current limiting power supply useful as part of the catheter system of the present invention.

Each of the electrode terminals 18 (or one of a pair of terminals in bipolar operation) is connected to an individual current source by wires 52. A resistance feedback controlling network and a constant current supply means as described above, may be contained in an electronic module within controller 32. The resistance feedback control can be composed of active electronic components to perform its intended function. By way of example, and not intending to limit the scope of the invention, a network composed of active circuit elements is illustrated in FIG. 9. Referring to FIGS. 1, 2, and 9, active control means are provided based on frequent measurements of resistance between each electrode 18' and the return electrode 16. If the measured resistance between any individual electrode 18' and return electrode 16 is greater than the preselected threshold level, then current is supplied to that electrode 18' during the next energizing period (e.g., time duration of several to several hundred milliseconds). In contrast, if the measured resistance is less than the preselected threshold level, then the current is interrupted (or significantly reduced) to that electrode 18' during the next energizing period. In this manner, the resistances between each electrode in the array are measured and used to select which electrodes are powered during the energizing period. The network can be easily modified for bipolar operation by eliminating the guidewire connection 16 and providing a number of return connectors to be paired with active connectors for the paired electrode terminals.

The desired temperature rise of the atheromatous plaque to effect desired recanalization is of the order of 10° to 60° C. Based on the above calculation, a 10° to 60° C. increase in the temperature of the atheromatous plaque using the apparatus and method of the present invention will result in a corresponding rise of blood or vessel wall temperature in the range of only about 1° to 6° C. as a result of limitation of current flowing directly therethrough.

Once a sufficient temperature rise is accomplished in the atheromatous plaque, the mechanical strength of the said mass is substantially reduced in the localized region surrounding the tip 12 of catheter 10. This allows the catheter 10 to be advanced incrementally through the plaque by applying a longitudinal force on the portions of the catheter 10 external to the patient. This force is transmitted along the length of the catheter 10 to the tip region 12 to create a "boring pressure" sufficient to penetrate the plaque 58. As the blood vessel wall is not equivalently heated or softened, the catheter will preferentially advance through the plaque 58 following a path of its own creation.

Heating by the catheter of this invention can also be controlled by a temperature feedback control mechanism. The temperature of the atheroma in contact with the tip 12 is sensed by temperature sensing elements, such as thermocouple pairs 48 as shown in FIG. 3. A feedback control loop in the power source 32 allows for the adjustment of the necessary voltage applied so the required temperature rise in the atheroma is accomplished. Conversely, by continuously monitoring the temperature of the atheroma being heated, the appropriate voltage level may be continuously and automatically adjusted so that the user-selected temperature is never exceeded.

While the above description provides a full and complete disclosure of a preferred embodiment of the invention, various modifications, alternative constructions, and equivalents may be employed. For example, the power could be communicated to the electrodes by wires imbedded in the catheter wall. Also, temperature sensing may be performed using fiber optics with infrared sensing technique, a thermocouple, a thermistor or other temperature sensing means. Alternatively, by proper selection of metals used for (1) the multiplicity of electrodes and leads (e.g., Constantan) and (2) the guidewire (e.g., steel) each individual electrode can function as a thermocouple in conjunction with the singular guidewire. Measurement of the direct current voltage between the guidewire and the multiplicity of electrodes would then indicate the maximum temperature at any location on the catheter tip. This information could then be used in the feedback control loop as described above to ensure an improved safe upper limit on the operating temperature during use of the apparatus of the present invention.

Figure 10:
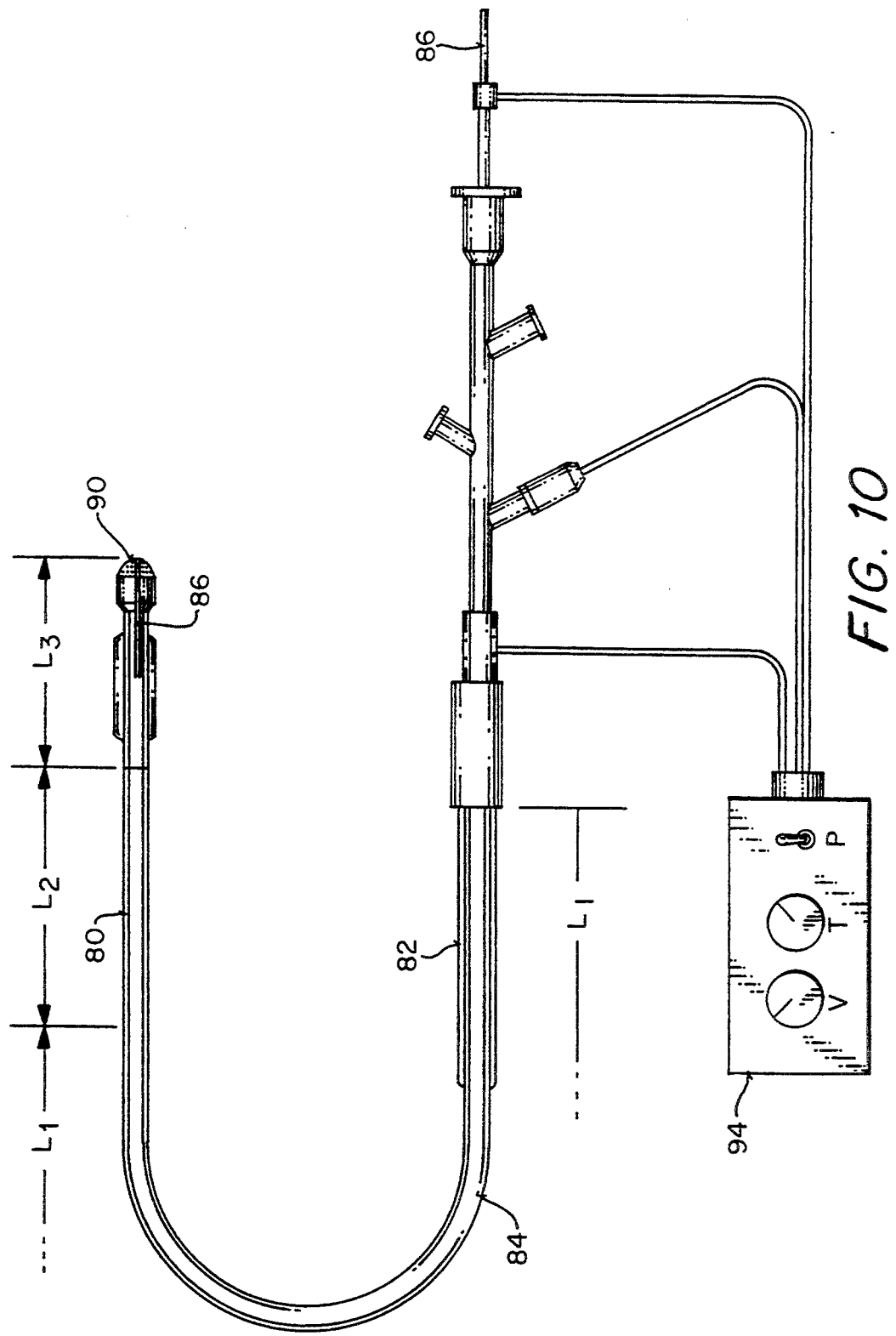
FIG. 10 is a second embodiment of a catheter system constructed in accordance with the principles of the present invention.
Figure 10A:
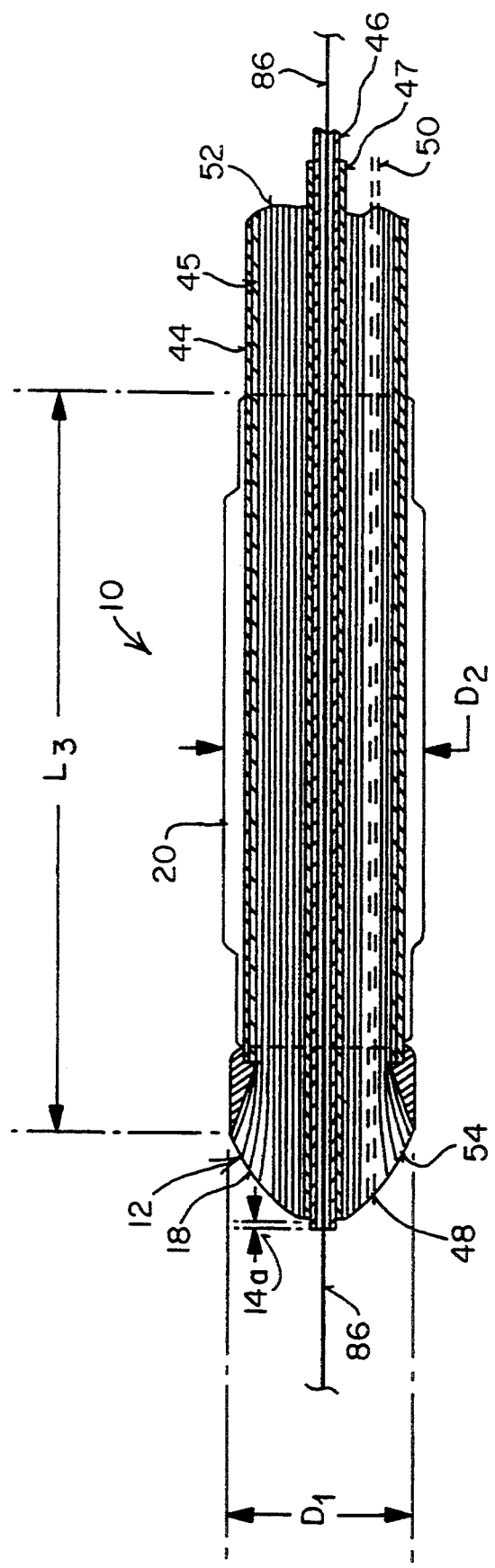
FIG. 10A is a sectional view of the distal end of the catheter of FIG. 10.

An alternative embodiment of the catheter of this invention is shown in FIGS. 10 and 10A. In this embodiment, the catheter 80 is substantially similar in construction to that of FIG. 1, except that a second (common) electrode 82 is provided on the body 84 of the catheter shaft instead of (or in combination with) the guidewire being the second electrode. During use of the catheter 80 in therapy, this second electrode 82 is intended to be in electrical contact with the blood in the artery. The location of the second electrode 82 is shown to be near the proximal end of the catheter 80, but could also be disposed more distally.

Still referring to FIGS. 10 and 10A guidewire 86 is connected to the current-limiting circuitry in power source 94 in a manner similar to the electrical connection of tip electrodes 90. During use of the catheter 80, the guidewire 86 becomes an additional electrode working in conjunction with the other tip electrodes. In this embodiment, no offset between the guidewire 86 and electrode array 90 is required.

The distal tip 12 includes a tapered forward surface and an outer perimeter having a diameter $D_1$. The tapered surface includes the electrodes 18 of the electrode array, and the outer perimeter is larger than the diameter of the catheter body which lies immediately proximal to the tip 12. In this way, a protected region is formed proximally of the tip, in which region a variety of interventional and/or diagnostic structures can be disposed. As illustrated in FIG. 10A, a balloon 20 is disposed behind the tip 12, wherein the combined diameter $D_2$ of the catheter body and the uninflated balloon is less than outer perimeter of the tip. Optionally, the diameter of the catheter body can be increased proximally of the balloon 20.

Figure 11:
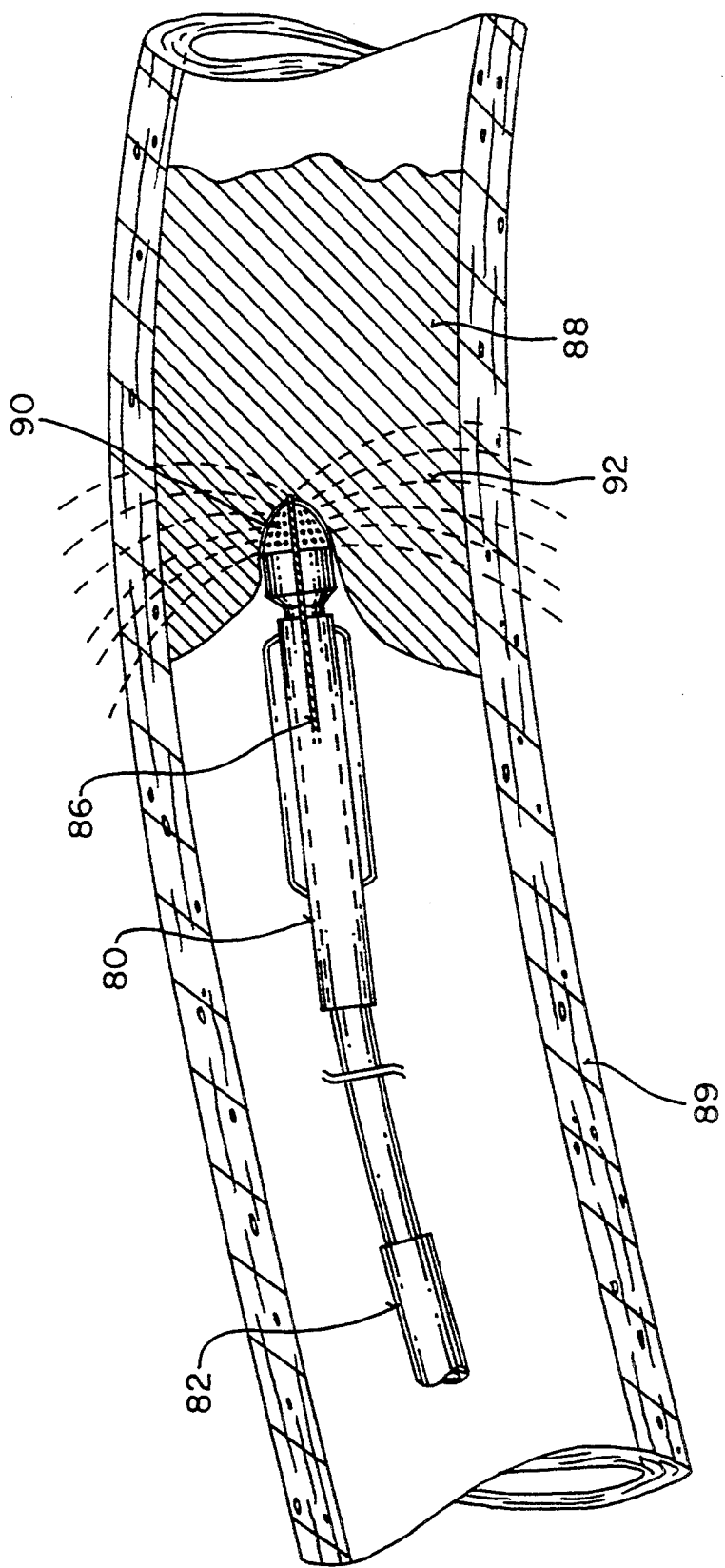
FIG. 11 illustrates use of the catheter of FIG. 10 in the recanalization of a stenosed region within a blood vessel according to the methods of the present invention.

Referring now to FIG. 11, the catheter 80 is advanced over the guidewire 86 to the site of a total occlusion (atheromatous mass) 88 in the artery 89. The electrode array 90 and the guidewire 86 are connected to the power source 94 (FIG. 10) and the second (common) electrode 82 is connected to an opposite polarity terminal of the power source. By applying power to the electrodes 90 and 82, current flux lines 92 are formed and distributed in the occlusion 88. The highest current density exists at the immediate vicinity of the tip electrode array 90, thereby producing maximum heating of the atheroma in contact with the catheter tip. A return path for the electrical current from the tip electrodes 90 to the second electrode 82 is defined through the blood in the blood vessel, the blood vessel wall, and/or the surrounding tissue. The second (common) electrode 82 is designed to be long with a large surface area to ensure low density of current flux lines at said second electrode and consequently, minimal temperature rise of the tissue or blood in contact therewith. It will be appreciated that the common electrode could be provided by the guidewire 86 as an alternative to or in combination with the second common electrode 82.

As the current passes through, the temperature of the atheromatous material 88 is raised, thereby softening the occlusion. The catheter 80 is advanced along the guidewire 86 through the softened atheroma until the vessel is recanalized. A final recanalization step can then be performed by balloon dilatation or other available therapeutic techniques.

Figure 12:
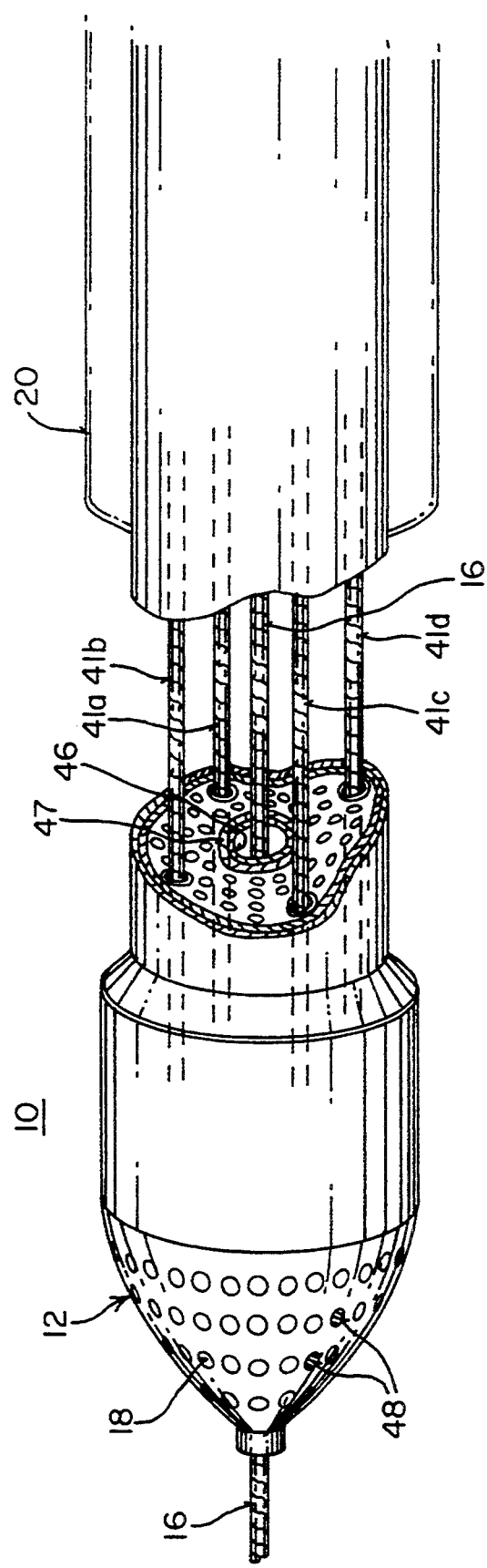
FIG. 12 illustrates a third embodiment of a catheter constructed in accordance with the principles of the present invention in combination with steering wires shown in cut away section.
Figure 12A:
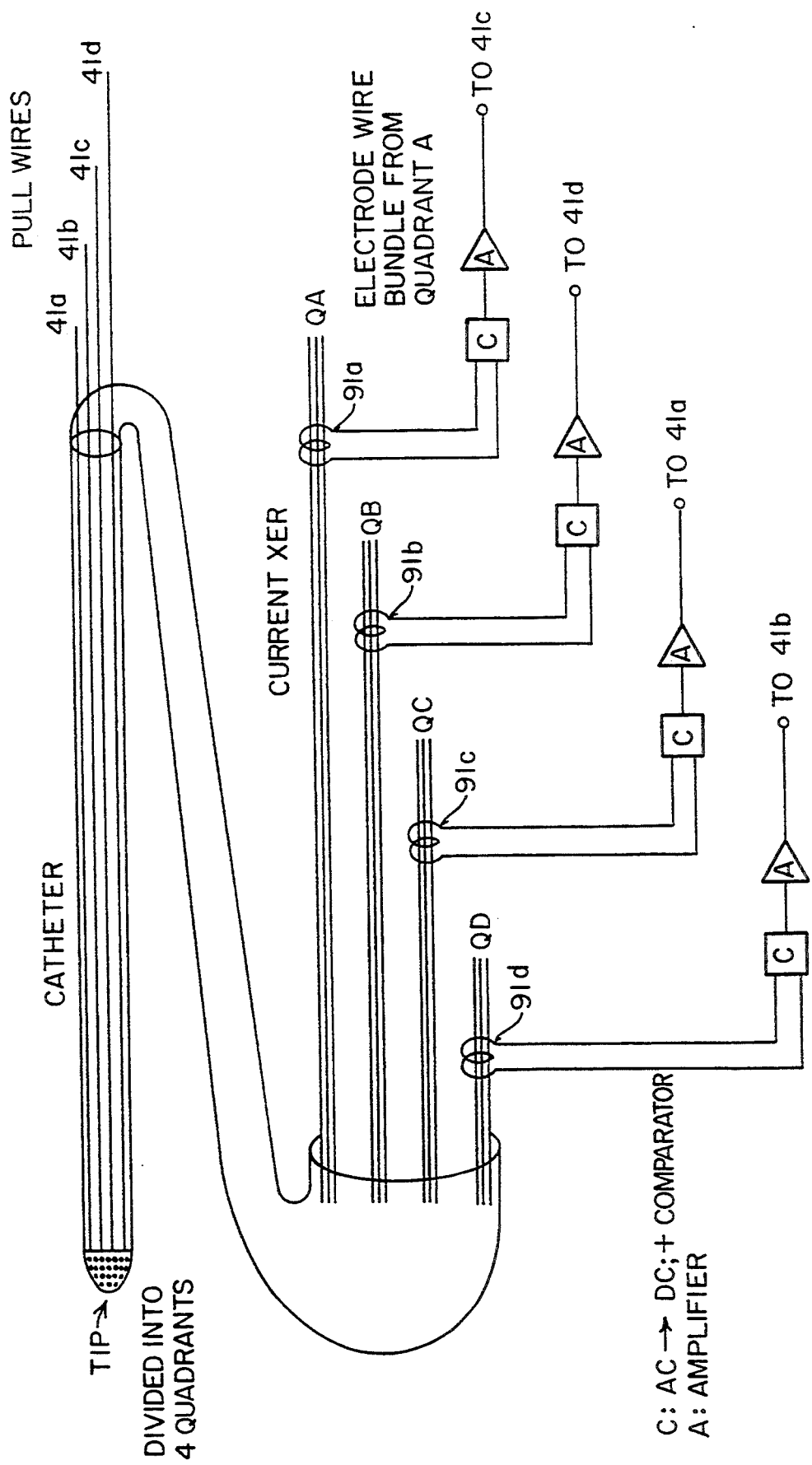
FIG. 12A provides a schematic view of electronic means for actuation of the steering wires illustrated in FIG. 12.
Figure 12B:
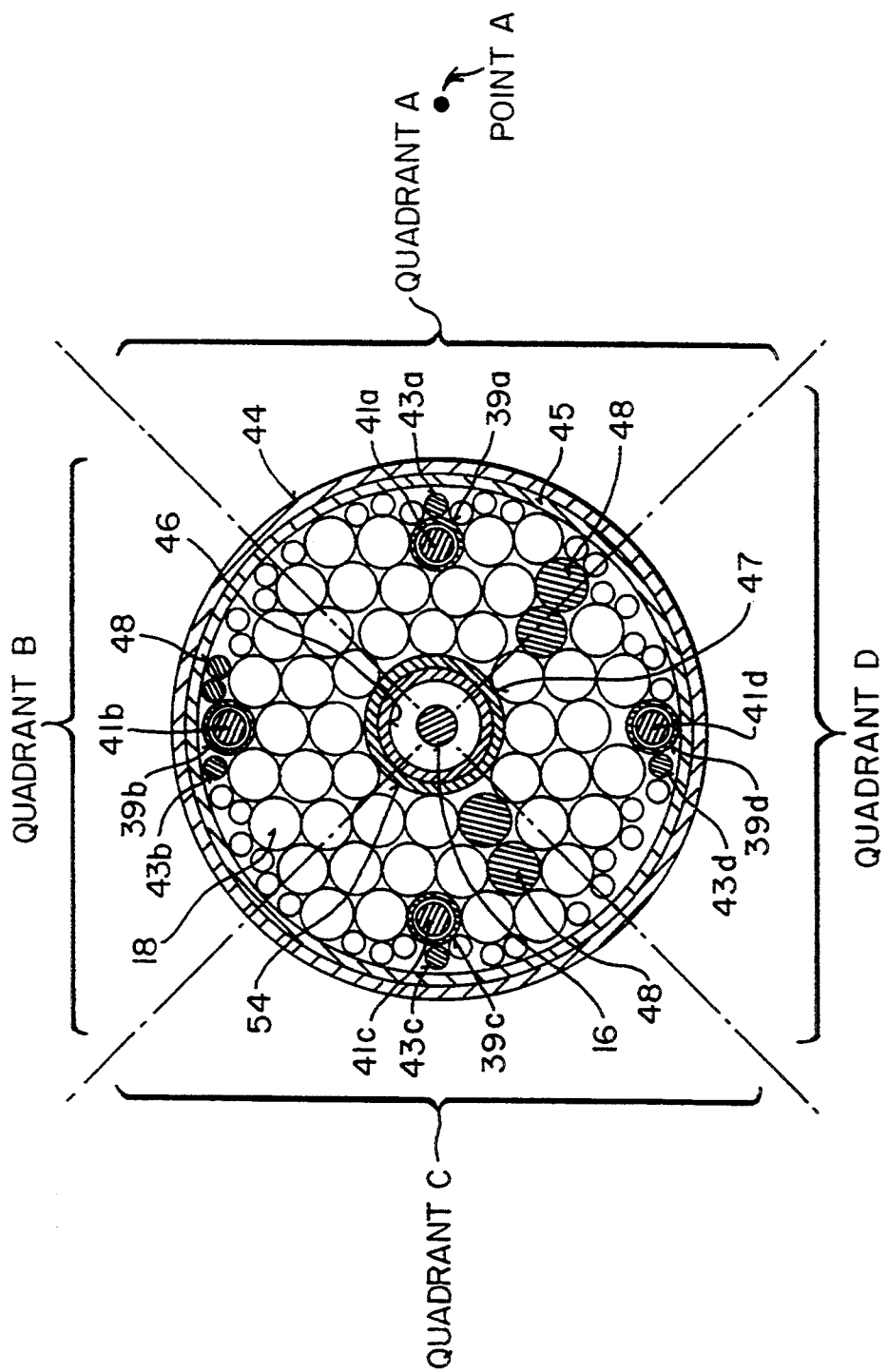
FIG. 12B is an end view of the distal tip of the catheter of FIGS. 12 and 12A illustrating approximate locations of the steering wires.

Referring now to FIGS. 12, 12A, 12B and 12C, catheter 10 can also incorporate a steering means which can change the curvature of the distal portion of catheter 10, thereby effecting a change in the direction of catheter 10 as it advances through lumen 89. By way of example, and not intending to limit the scope and spirit of this invention, FIGS. 12 and 12B illustrate one preferred embodiment of said steering means comprising four steering actuation wires 41A, 41B, 41C and 41D equispaced within four quadrants of catheter 10. Said actuation wires 41 may be constructed, for example, of nickel-titanium alloys that exhibit a shape memory characteristic. Such shape memory alloys change their internal structure at a certain temperature and can be caused, for example, to contract when heated above a predetermined (composition dependent) temperature. Such actuation wires are commercially available in diameters ranging from 0.001 to 0.010 inch from Dynalloy, Inc. (Irvine, Calif.).

In a preferred embodiment of the present invention illustrated in FIGS. 12 and 12B, actuation wires 41 are positioned near the outer perimeter of catheter 10 and have a diameter selected within the range from 0.002 to 0.008 inch. Said steering actuation wires 41 are caused to contract by the application of sufficient current to heat a given actuation wire 41 above the transition temperature, thereby effecting contraction of a that actuation wire 41 and consequently inducing a curvature in the distal portion of catheter 10. The shape-memory alloy composition can be selected to obtain a transition (contraction) temperature above body temperature but below temperatures that would produce an unwanted temperature rise in the catheter and/or surrounding tissue. For the intended use in the present invention a threshold transition (contraction) temperature of 45° to 90° C. may be selected, more preferably in the range of 45° to 60° C.

In a preferred embodiment of the present invention, the steering means described above can be controlled based on the resistance measurements performed at the tip 12 of catheter 10. By way of example and referring to FIGS. 10, 12 and 12B, the distal portion of catheter 10 may be partitioned into four quadrants as shown in FIG. 12B with one actuation wire 41 within each of the four quadrants. By proper selection of the relative stiffness of catheter sections $L_1$, $L_2$ and $L_3$ and the contractile force of actuation wires 41 (as determined by the alloy composition and actuator wire diameter), the passage of an electrical current having a level appropriate for the wire diameter and threshold temperature selected through a particular actuation wire causes the distal portion of catheter 10 to bend or curve. For example and referring to FIG. 12B, if actuation wire 41A is heated to the threshold temperature by the passage of electrical current therethrough, said actuation wire 41A will contract and the catheter will be deflected and will curve towards point A. The axial movement of the contracting actuating wire can be accommodated by placement of each actuation wire within an electrically insulating, low friction sleeve 39 (e.g., Teflon® tubing).

One preferred embodiment for automatically steering the catheter 10 through a lumen is illustrated schematically in FIG. 12A. The combined current flow to the ensemble of electrodes 18 within each of the four quadrants at the tip 18 of catheter 10 can be monitored using four independent current-measuring means 91. If the combined current flow from the electrodes within quadrant C is substantially lower than the other three quadrants A, B and D, this indicates that the tip portion of catheter 10 defined within quadrant C is in contact with a lower resistance material (e.g., vessel wall). The result of this measurement can be used, through appropriate signal processing and amplification, to apply electrical current to the opposite actuation wire 41A as illustrated in FIG. 12B. According to this embodiment of the present invention, the effect of quadrant 41C of the tip 18 of catheter 10 being exposed to low resistance media (e.g., blood vessel wall) is to cause the catheter to deflect or "steer" away from said region of lower electrical resistance, thereby maintaining catheter 10 in the more central portions of the lumen and away from the wall of the lumen.

Figure 12C:
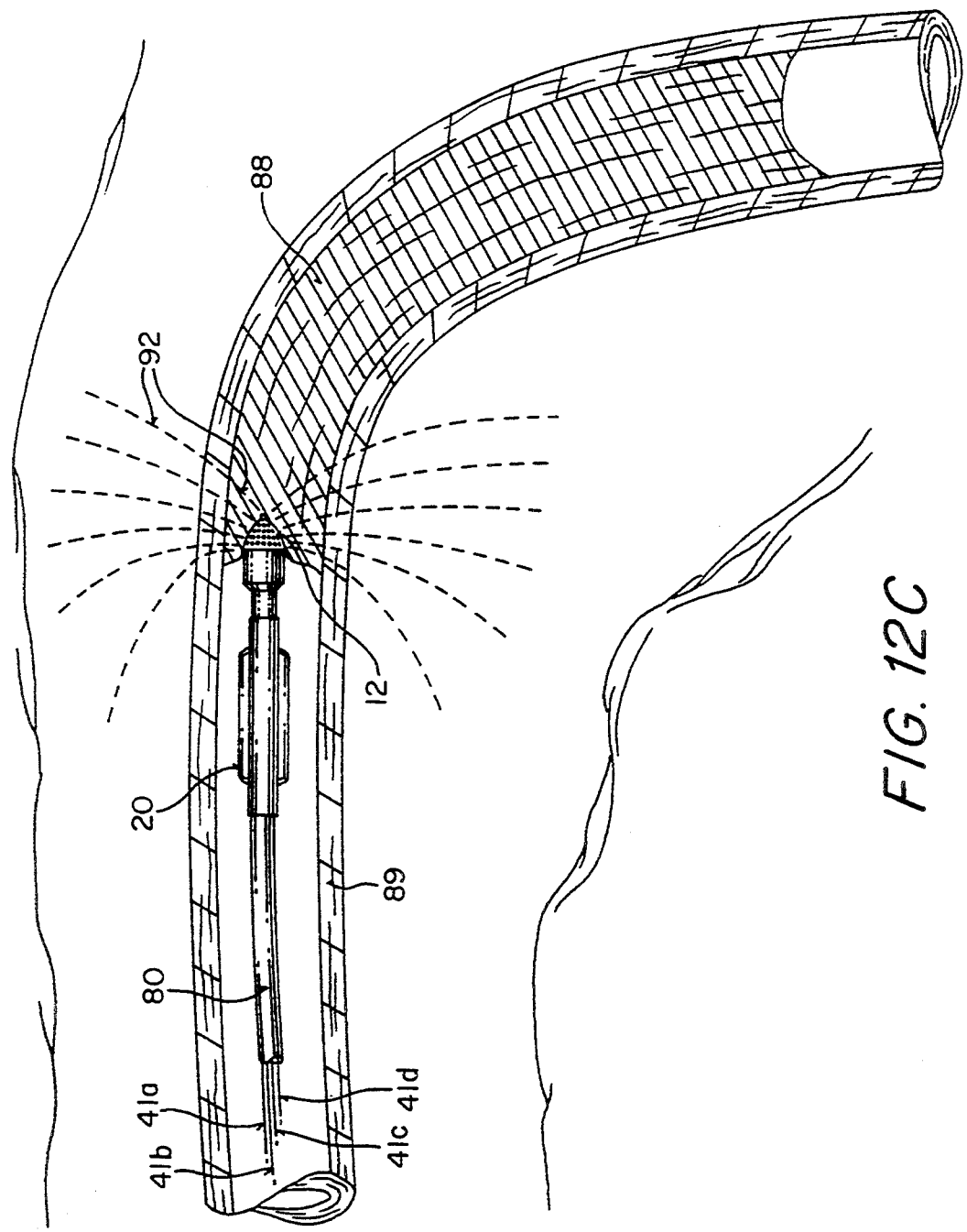
Figure 13:
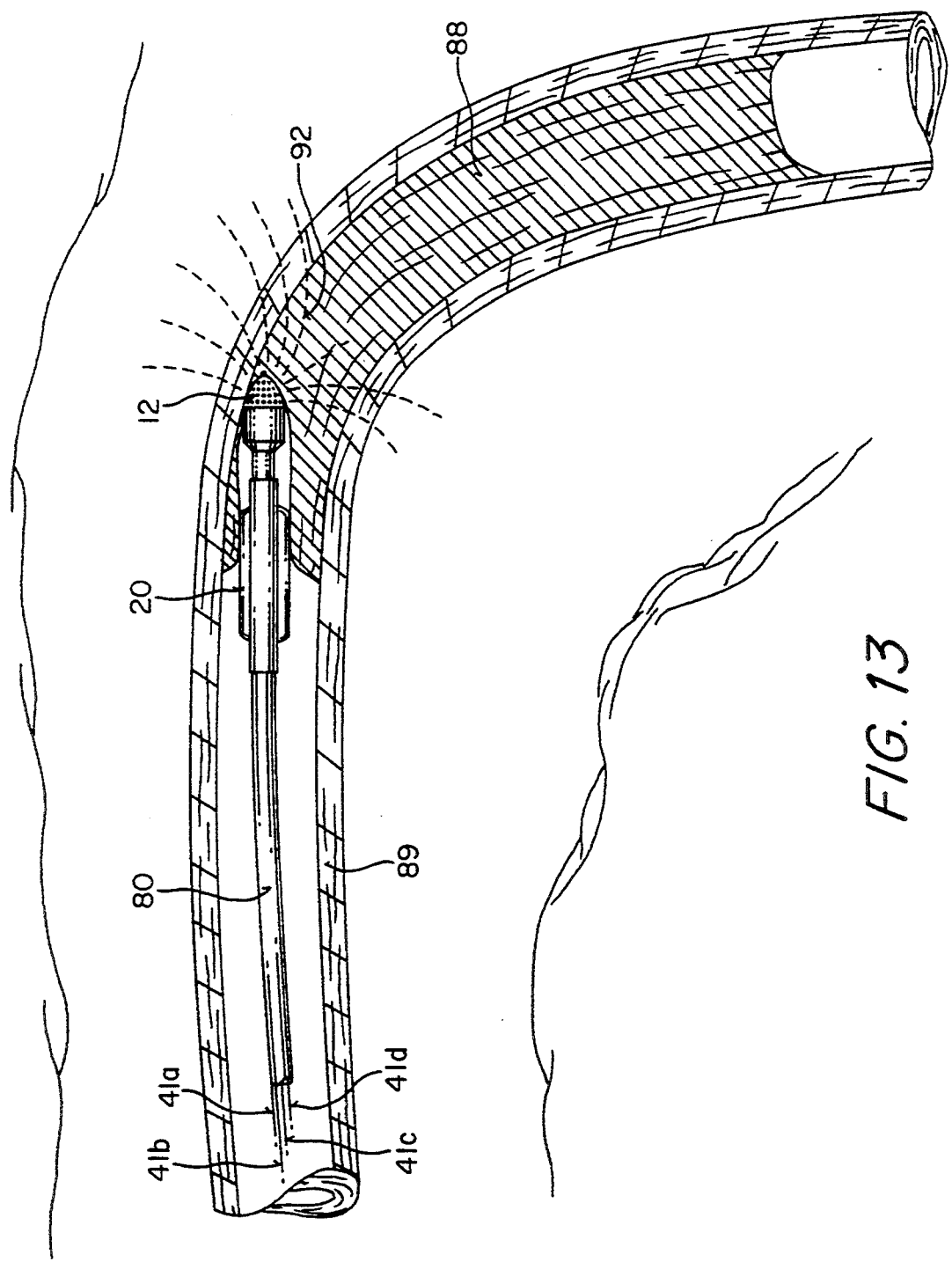

FIGS. 12C, 13, 14 and 15 illustrate how catheter 80 can be applied to recanalize a curved blood vessel 89 occluded with atheromatous media 88. As shown in FIG. 12C, the tip 12 of catheter 80 begins to advance through atheromatous media 88 using the electrical current flux 92 induced heating and softening effects described herein. Since the electrodes at tip 12 of catheter 80 in all four quadrants are exposed to relatively high resistance (e.g., atheromatous media 88), none of the four actuation wires are energized (heated) and consequently the catheter 80 proceeds in a substantially straight direction. Referring now to FIG. 13, the tip 12 of catheter 80 has now advanced into wall 89 of the blood vessel due to the curvature of the vessel wall. As described above, those electrodes 18 at the tip of catheter 80 in the one or two quadrants in contact with the lower resistance blood vessel wall 89 will, according to the teachings of this invention, deliver a reduced current to the electrodes 18 in those said one or two quadrants. By way of example, assume that electrodes 18 at the tip 12 of catheter 80 in quadrant A are predominantly in contact with blood vessel wall 89. As a result, the combined current flow in the leads 52 to said electrodes 18 in quadrant A will be reduced. According to the electrical schematic in FIG. 12A, a reduction in the combined current flow in quadrant A will cause actuation wire 41C to be energized and contract, in turn causing the distal portion of catheter 80 to bend away from the vessel wall 89 as illustrated in FIG. 14 and 15. Once the tip 12 of catheter 80 is deflected away from the vessel wall 89 as shown in FIG. 14, the actuation wires are no longer energized and the advance of the catheter 80 continues in a substantially straight direction.

FIG. 15 illustrates one preferred embodiment of the implementation of actuation wires 41 within catheter 80. By way of example, the actuation wires 41 may be contained within an electrically insulating sleeve, 39. The distal ends 45 of said actuation wires 41 are enlarged as shown in FIG. 15 in order to serve as an anchor within the tip region 12 of catheter 80. Electrically conducting wires 43 (e.g., copper wires) coated with electrical insulation 47 are electrically connected to the distal ends 45 of actuation wires 41 by conventional joining methods (e.g., welding, brazing, soldering). Attachment of the actuation wires 41 to low resistance lead wires 43 provides the means for the application of voltage between the actuation wires 41 and the lead wires 43 sufficient to produce heating and, in turn, sufficient temperature rise in the actuation wire 41 to effect the contraction of said actuation wire 41 required for steering of the tip 12 of catheter 80.

Alternatively, the steering of the distal end 12 of catheter 80 may be effected by selectively delivering current to one or more actuation wires based on "feedback" from (1) the measurement of parameters at the tip 12 of the catheter 80 (e.g., temperature coefficient of resistance, dielectric constant, optical properties) or (2) physical observations of catheter 80 in lumen 89 using, for example, radiographic or ultrasonic visualization means.

Figure 16:
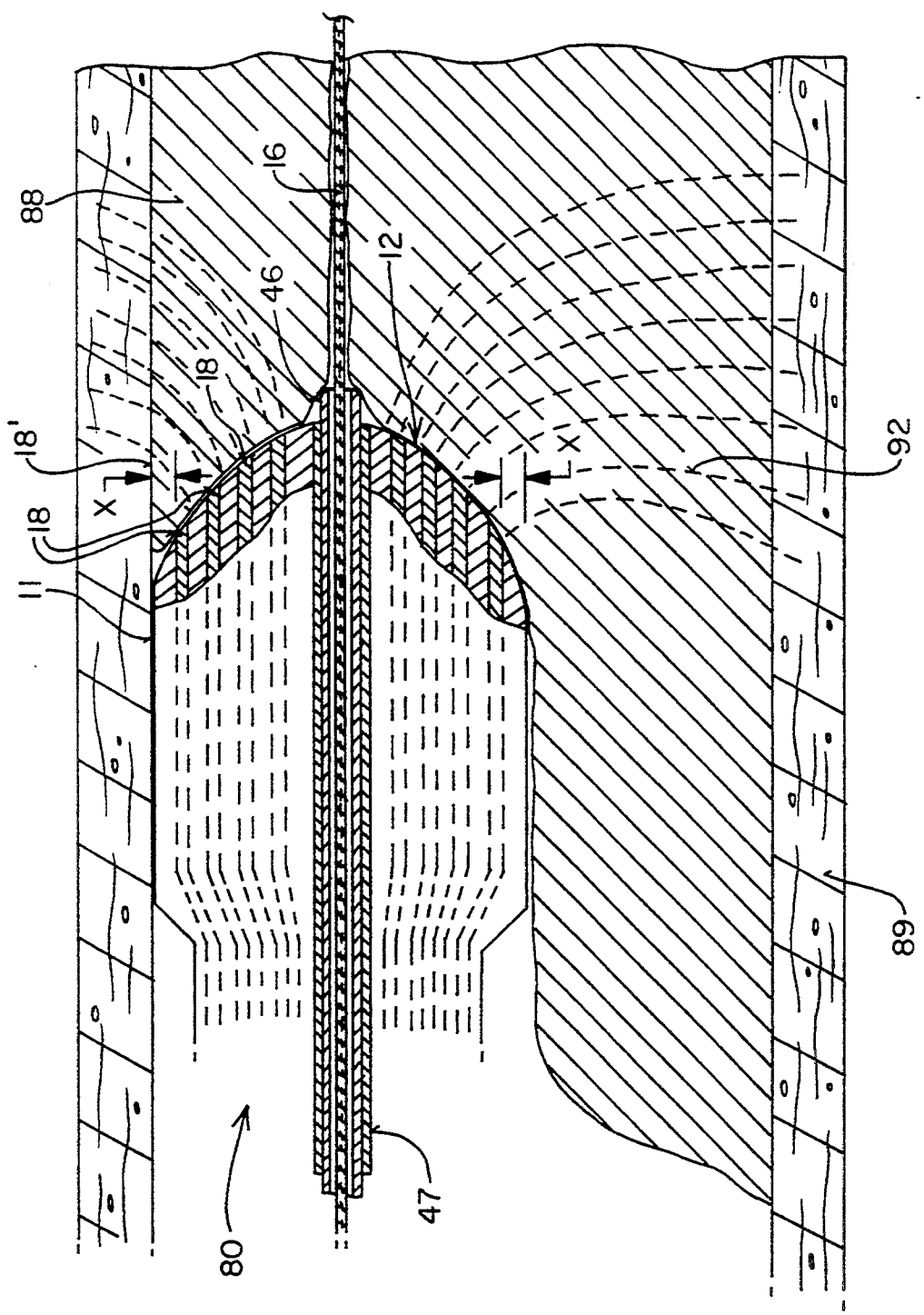
FIG. 16 illustrates a catheter according to the present invention in which the electrodes of the array are set back some distance from the outer edge of the distal tip.

Another preferred embodiment of the present invention is illustrated in cross-sectional view in FIG. 16. In this illustration, the tip 12 of catheter 80 is in contact with the wall 89 of the blood vessel. The exposed ends of electrodes 18 are shown distributed over the frontal surface of catheter tip 12 but recessed a distance of not less than X from the perimeter 11 of the catheter tip 12. By recessing the outermost electrodes 18' away from the perimeter 11 of the catheter tip 12, heating of vessel wall 89 can be minimized due to the reduction of current flux 92 with distance from the exposed electrode tip 18 or 18'. It is well known that the current flux from a circular electrode in contact with a conductive media is approximately inversely proportional to the square of the distance from the electrode surface. By way of example, for electrode 18 diameter of 0.004 inch, the average current density at a distance of two diameters or 0.008 inch from the electrode is approximately one eighth the average current flux at the surface of the electrode. The preferred distance X for the separation of the nearest electrode 18' to the perimeter 11 of catheter tip 12 is in the range 1 to 4 electrode diameters and more preferably in the range 1.5 to 2.5 electrode 18' diameters. For the present example involving 0.004 inch diameter electrodes, the preferred separation distance X would be in the range of 0.006 inch to 0.010 inch.

Preferred embodiments will include an enlarged distal tip in the region housing the electrodes. Referring in particular to FIG. 16, the enlarged distal tip is advantageous in that it shields the inflatable balloon 20 from tearing or damage as the catheter body advances into the occluded region. To achieve this, the enlarged tip should preferably have a diameter at least as great as the diameter of the uninflated balloon dispose about the catheter body. Although it is preferable that the enlarged portion of the catheter body be that portion housing the electrodes, a different region could serve the same purpose as long as it is sufficiently large and located at a point distal to the balloon.

Although the foregoing invention has been described in detail for purposes of clarity of understanding, it will be obvious that certain modifications may be practiced within the scope of the appended claims.

What is claimed is:

1. A catheter system comprising:
    a catheter body having a proximal end and a distal end;
    an electrode array disposed near the distal end of the catheter body, said array including a plurality of electrically isolated electrode terminals disposed over a contact surface;
    means for applying a high frequency voltage between the electrode array and at least one common electrode, wherein current flow to each electrode terminal is selectively controllable; and
    means for steering the catheter by changing the curvature of the catheter body between the proximal and distal ends in response to changes in current flow to electrode terminals in different regions of the electrode array.

2. The catheter system of claim 1, wherein the steering means comprises a plurality of steering wires disposed in the catheter body and connected to the distal end thereof, wherein the catheter body is steerable by selective contraction of at least one of the wires.

3. The catheter system of claim 2, wherein the steering wires are disposed within low-friction sleeves.

4. The catheter system of claim 2, wherein the steering means comprises at least four steering wires, one wire in each of four quadrants of the catheter body.

5. The catheter system of claim 2, wherein the steering wires are composed of a shape-memory alloy, and wherein the wires contract when heated above a predetermined transition temperature.

6. The catheter system of claim 2, wherein contraction of the steering wires is effected by the selective conduction of electrical current through the steering wires.

7. The catheter system of claim 6, further comprising means for selectively increasing current through each steering wire in response to a rise in current flow between the individual electrodes in the region of the array disposed opposite to the wire and the common electrode.

8. The catheter system of claim 1, wherein the catheter body includes regions of differing stiffness.

9. The catheter system of claim 8, wherein the catheter body includes at least three regions of differing stiffness, wherein the catheter body increases in stiffness from the distal to the proximal end.

10. The catheter system of claim 1, wherein the common electrode is selected from the group consisting of an electrode formed on the exterior surface of the catheter body, a guidewire, and a paired isolated electrode terminal.

11. A catheter comprising:
    a catheter body having proximal and distal ends, a proximal region, and a distal tip, wherein the distal tip of the catheter body has a cross-sectional area greater than that of the proximal region whereby an annular protected region is formed proximally of the tip; and
    a plurality of isolated electrode terminals formed over a distal surface of the distal tip of the catheter body.

12. The catheter of claim 11, wherein the structure is an angioplasty balloon and the combined diameter of the protected region and the balloon in its uninflated state is less than the diameter of the distal tip.

13. A catheter system comprising:
    a catheter body having a proximal end, a distal end, and a forwardly disposed contact surface;
    an electrode array disposed near the distal end of the catheter body, said array including a plurality of electrically isolated electrode terminals disposed over the contact surface; and
    means for applying a high frequency voltage between the electrode array and a return electrode selected from the group consisting of a common electrode and a paired isolated electrode within the array, wherein current flow to each electrode terminal is selectively controllable, and wherein the diameter of the catheter body is greater in the vicinity of the contact surface than the diameter of the catheter body in a location proximal to the electrode array.

14. The catheter system of claim 13, further comprising:
    an inflatable balloon disposed about the catheter body at a location proximal to the electrode array, wherein the diameter of the uninflated balloon disposed about the catheter body is less than the diameter of the catheter body in a location distal to the balloon.

15. The catheter system of claim 13, wherein the distal end of the catheter is formed to have a tapered forward surface and an outer perimeter, wherein the electrode array is formed over the tapered forward surface and the peripheral shank has the greater diameter.

16. A catheter system comprising:
    a catheter body having a proximal end a distal end, and a distally exposed contact surface having an outer perimeter;
    an electrode array disposed near the distal end of the catheter body, said array including a plurality of electrically isolated electrode terminals disposed over a portion of the contact surface; and
    means for applying a high frequency voltage between the electrode array and a return electrode selected from the group consisting of a common electrode and a paired isolated electrode within the array, wherein current flow to each electrode is selectively controllable, and wherein the electrodes closest to the perimeter of the contact surface are laterally set back at some distance from the perimeter.

17. The catheter system of claim 16, wherein the electrodes have a circular cross-section and wherein the electrodes are set back a distance from the perimeter equal to or greater than one electrode diameter.

18. A method for advancing a catheter through a body lumen, the method comprising the steps of:
    advancing the catheter into the lumen to engage a forwardly disposed contact surface against an atheromatous mass;
    applying a high frequency voltage through an electrode array disposed over the contact surface;
    changing the curvature of the catheter using steering wires disposed along the length of the catheter so that the electrode array remaining engaged against the atheromatous mass as the contact surface advances through the atheromatous mass in the body lumen.

19. The method of claim 18, wherein the step of controlling the curvature of the catheter is performed by selectively contracting one or more of the steering wires.

20. The method of claim 19, wherein the step of selectively contracting the steering wires is performed by selectively heating one or more of the steering wires.

21. The method of claim 19, wherein the step of selectively contracting the steering wires is performed by conducting electrical current selectively through one or more of the steering wires.

22. The method of claim 21, wherein the conduction of current through a steering wire is selectively increased in response to a rise in current flow to the individual electrodes in the region of the array opposite to the wire.

23. The method of claim 22, wherein current is supplied to the electrodes of the array through current supply wires in the catheter body, and wherein the step of conducting current through the steering wires includes sensing the current within the current supply wires and controlling the current in the steering wires based on the sensed current.

24. A catheter system comprising:
a catheter body having a proximal end and a distal end;
an electrode array disposed near the distal end of the catheter body, said array including a plurality of electrically isolated electrode terminals disposed over a contact surface;
means for applying a high frequency voltage between the electrode array and a common electrode selected from the group consisting of an electrode formed on the exterior surface of the catheter body, a guidewire, and a paired isolated electrode terminal, wherein current flow to each electrode terminal is selectively controllable; and
means for steering the catheter by changing the curvature of the catheter body between the proximal and distal ends.

25. The catheter system of claim 24, wherein the steering means comprises a plurality of steering wires disposed in the catheter body and connected to the distal end thereof, wherein the catheter body is steerable by selective contraction of at least one of the wires.

26. The catheter system of claim 25, wherein the steering wires are disposed within low-friction sleeves.

27. The catheter system of claim 25, wherein the steering means comprises at least four steering wires, one wire in each of four quadrants of the catheter body.

28. The catheter system of claim 25, wherein the steering wires are composed of a shape-memory alloy, and wherein the wires contract when heated above a predetermined transition temperature.

29. The catheter system of claim 25, wherein contraction of the steering wires is effected by the selective conduction of electrical current through the steering wires.

30. The catheter system of claim 25, further comprising means for selectively increasing current through each steering wire in response to a rise in current flow between the individual electrodes in the region of the disposed opposite to the wire and the common electrode.

31. The catheter system of claim 24, wherein the catheter body includes regions of differing stiffness.

32. The catheter system of claim 21, wherein the catheter body includes at least three regions of differing stiffness, wherein the catheter body increases in stiffness from the distal to the proximal end.

33. A catheter comprising:
a catheter body having proximal and distal ends, a proximal region, and a distal tip, wherein the distal tip of the catheter body has a cross-sectional area greater than that of the proximal region whereby an annular protected region is formed proximally of the tip;
a plurality of isolated electrode terminals formed over a distal surface of the distal tip catheter body; and
a balloon disposed within the annular protected region wherein the combined diameter of the protected region and the balloon in its uninflated state is less than the diameter of the distal tip.

34. A catheter system comprising:
a catheter body having a proximal end and a distal end;
an electrode array disposed near the distal end of the catheter body, said array including a plurality of electrically isolated electrode terminals disposed over a contact surface;
means for applying a high frequency voltage between the electrode array and a return electrode selected from the group consisting of a common electrode and a paired isolated electrode within the array, wherein current flow to each electrode terminal is selectively controllable, and wherein the diameter of the catheter body is greater in the vicinity of the electrode array than the diameter of the catheter body in a location proximal to the electrode array; and
an inflatable balloon disposed about the catheter body at a location proximal to the electrode array, wherein the diameter of the uninflated balloon disposed about the catheter body is less than the diameter of the catheter body in a location distal to the balloon.

35. The catheter system of claim 34, wherein the distal end of the catheter has a tapered forward surface and an outer perimeter, wherein the electrode array is formed over the tapered forward surface and the perimeter has a greater diameter than that of the proximal catheter body.

* * * * *